(12) United States Patent
Cordero Gomez Del Campo et al.

(10) Patent No.: US 11,369,763 B2
(45) Date of Patent: Jun. 28, 2022

(54) RESPIRATORY VENTILATORY DEVICE AND METHOD OF OPERATING SAME

(71) Applicant: Soco International LLC, Las Vegas, NV (US)

(72) Inventors: Jose Luis Esteban Cordero Gomez Del Campo, Irapuato (MX); Jorge Antonio Cordero Gomez del Campo, Las Vegas, NV (US)

(73) Assignee: Soco International LLC, Las Vegas, NV (US)

( * ) Notice: Subject to any disclaimer, the term of this patent is extended or adjusted under 35 U.S.C. 154(b) by 0 days.

(21) Appl. No.: 17/387,537

(22) Filed: Jul. 28, 2021

(65) Prior Publication Data

US 2022/0031985 A1 Feb. 3, 2022

Related U.S. Application Data

(60) Provisional application No. 63/059,636, filed on Jul. 31, 2020.

(51) Int. Cl.
*A61M 16/20* (2006.01)
*A61M 16/00* (2006.01)
*A61M 16/08* (2006.01)

(52) U.S. Cl.
CPC ...... *A61M 16/024* (2017.08); *A61M 16/0066* (2013.01); *A61M 16/0816* (2013.01); *A61M 16/208* (2013.01)

(58) Field of Classification Search
CPC ....... A61K 33/00; A61K 9/007; A61M 11/06; A61M 15/0068; A61M 15/0076; A61M 15/009; A61M 16/00; A61M 16/0003; A61M 16/0009; A61M 16/0051; A61M 16/0057; A61M 16/0066; A61M 16/0069; A61M 16/0075; A61M 16/0081; A61M 16/01; A61M 16/024; A61M 16/04; A61M 16/06; A61M 16/0666; A61M 16/0808; A61M 16/0816; A61M 16/0833; A61M 16/085; A61M 16/0875; A61M 16/0883; A61M 16/0891; A61M 16/10; A61M 16/1005; A61M 16/1015; A61M 16/104; A61M 16/105; A61M 16/107; A61M 16/1075; A61M 16/12; A61M 16/122; A61M 16/16; A61M 16/20; A61M 16/201; A61M 16/202; A61M 16/203;

(Continued)

(56) References Cited

U.S. PATENT DOCUMENTS 2,924,215 A * 2/1960 Goodner ........... A61M 16/0009
128/205.13
3,523,527 A 8/1970 Foster (Continued)

*Primary Examiner* — Annette Dixon
(74) *Attorney, Agent, or Firm* — Howard & Howard Attorneys PLLC

(57) ABSTRACT

A respiratory ventilator device is described herein. The respiratory ventilator device includes an inhaled air assembly, an exhaled air assembly, and a control system operatively coupled to the inhaled air assembly and the exhaled air assembly. The inhaled air assembly is coupled to a patient respiratory circuit and configured to channel a volume of inhalation air to the patient's lungs to assist in patient inhalation. The exhaled air assembly is coupled to the patient respiratory circuit and configured to remove air from the patient's lungs to assist in a patient exhalation. The control system is configured to operate the respiratory ventilator system in an inhalation mode and an exhalation mode.

20 Claims, 17 Drawing Sheets

(58) Field of Classification Search
CPC . A61M 16/204; A61M 16/205; A61M 16/22; A61M 2016/0015; A61M 2016/0021; A61M 2016/0027; A61M 2016/003; A61M 2016/0036; A61M 2016/0039; A61M 2016/102; A61M 2016/1025; A61M 2016/103; A61M 2016/1035; A61M 2202/0208; A61M 2202/0233; A61M 2202/0241; A61M 2202/025; A61M 2202/0275; A61M 2202/0283; A61M 2202/0291; A61M 2205/15; A61M 2205/18; A61M 2205/3334; A61M 2205/3344; A61M 2205/3355; A61M 2205/3368; A61M 2205/35; A61M 2205/50; A61M 2205/502; A61M 2205/52; A61M 2205/75; A61M 2230/42; A61M 2230/43; A61M 2230/432; A61M 2230/435; A61M 2230/437; G16H 20/10
See application file for complete search history.

(56) References Cited

U.S. PATENT DOCUMENTS

| | | | | |
|---|---|---|---|---|
| 3,789,837 | A | | 2/1974 | Philips et al. |
| 5,615,669 | A * | 4/1997 | Olsson | A61M 16/12 128/203.12 |
| 5,769,072 | A * | 6/1998 | Olsson | A61M 16/104 128/204.22 |
| 5,865,173 | A * | 2/1999 | Froehlich | A61M 16/024 128/204.23 |
| 5,871,009 | A * | 2/1999 | Rydgren | A61M 16/12 128/203.12 |
| 5,918,596 | A * | 7/1999 | Heinonen | A61M 16/12 128/204.21 |
| 6,474,333 | B1 * | 11/2002 | Heinonen | A61M 16/10 128/203.12 |
| 6,786,217 | B2 * | 9/2004 | Stenzler | A61M 16/203 128/204.23 |
| 7,201,166 | B2 * | 4/2007 | Blaise | A61M 16/12 128/203.12 |
| 7,523,752 | B2 * | 4/2009 | Montgomery | A61M 16/04 128/204.21 |
| 8,746,241 | B2 * | 6/2014 | Cavendish | A61M 16/0833 128/203.12 |
| 8,893,717 | B2 * | 11/2014 | Montgomery | A61M 16/04 128/204.21 |
| 2015/0273175 | A1 * | 10/2015 | Acker | A61M 16/20 128/203.14 |
| 2015/0273176 | A1 * | 10/2015 | Acker | A61M 16/06 128/202.22 |
| 2015/0314101 | A1 * | 11/2015 | Acker | A61M 16/024 128/203.14 |

* cited by examiner

RESPIRATORY VENTILATORY DEVICE AND METHOD OF OPERATING SAME

CROSS-REFERENCE TO RELATED APPLICATION

This application claims the benefit of Provisional Patent Application Ser. No. 63/059,636, filed Jul. 31, 2020, the disclosure of which is incorporated by reference in its entirety.

FIELD OF THE DISCLOSURE

The present invention relates to a respiratory ventilator device for use with patients.

BACKGROUND

Known treatment protocols for patients diagnosed with coronavirus disease 2019 (COVID-19) caused by a novel coronavirus includes the use of respirator ventilators to assist patients with breathing. The current need for ventilators and the worldwide shortage of these devices due to the spread of COVID-19 and related Pneumonia, added to the regular need for these devices for non-covid-19 related Pneumonia. Known respirator ventilators are costly, putting them beyond most of world population reach.

The present invention is aimed at one or more of the problems identified above.

SUMMARY OF INVENTION

In one aspect of the present invention, a respiratory ventilator device is provided. The respiratory ventilator device includes an inhaled air assembly, an exhaled air assembly, and a control system operatively coupled to the inhaled air assembly and the exhaled air assembly. The inhaled air assembly is coupled to a patient respiratory circuit and configured to channel a volume of inhalation air to a patient's lungs to assist in patient inhalation. The exhaled air assembly is coupled to the respiratory circuit and configured to remove air from the patient's lungs to assist in a patient exhalation. The control system is configured to operate the respiratory ventilator system in an inhalation mode and an exhalation mode. The control system operates the inhaled air assembly to generate a positive air pressure to channel the volume of inhalation air to the patient's lungs during the inhalation mode and operates the exhaled air assembly to generate a negative air pressure to remove the air from the patient's lungs during the exhalation mode.

In another aspect of the present invention, a method of operating a respiratory ventilator device is provided. The respiratory ventilator device includes an inhaled air assembly coupled between a supply of oxygenated air and a patient respiratory circuit and an exhaled air assembly coupled between the patient respiratory circuit and an exhaust air outlet connector assembly. The method includes operating the inhaled air assembly to generate a positive air pressure to channel a volume of inhalation air to the patient's lungs during an inhalation mode and operating the exhaled air assembly to generate a negative air pressure to remove the air from the patient's lungs during an exhalation mode.

BRIEF DESCRIPTION OF THE FIGURES

Non-limiting and non-exhaustive embodiments of the present invention are described with reference to the following figures. Other advantages of the present disclosure will be readily appreciated, as the same becomes better understood by reference to the following detailed description when considered in connection with the accompanying drawings wherein.

Corresponding reference characters indicate corresponding components throughout the several views of the drawings.

DETAILED DESCRIPTION

Figure 1:
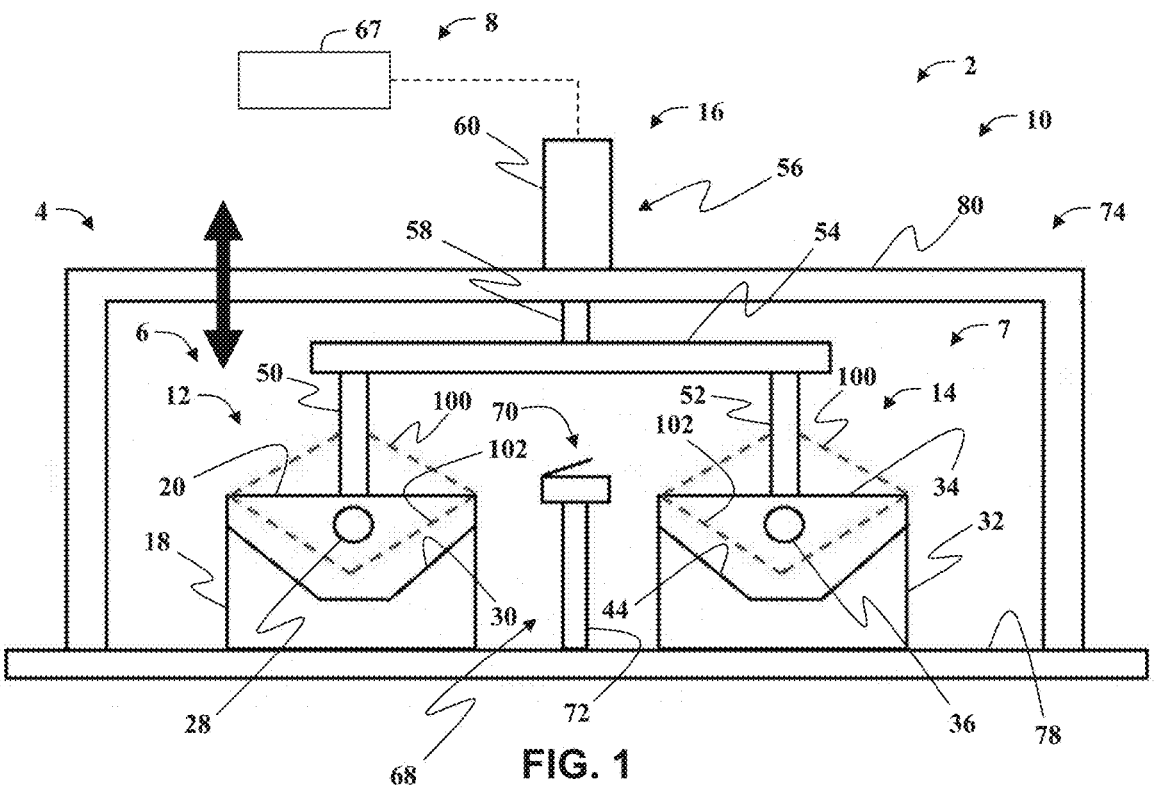
FIG. 1 is a front schematic view of a respirator ventilator device, according to the present invention.
Figure 2:
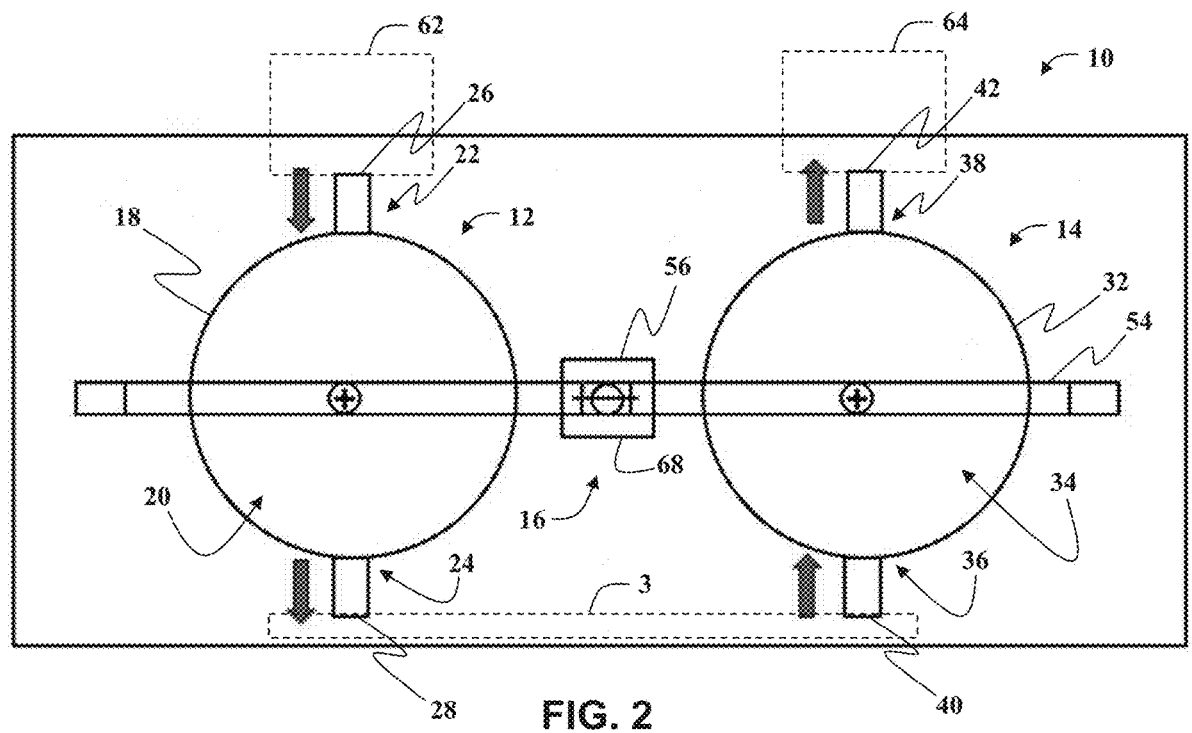
FIG. 2 is a top schematic view of the respirator ventilator device shown in FIG. 1.
Figure 3:
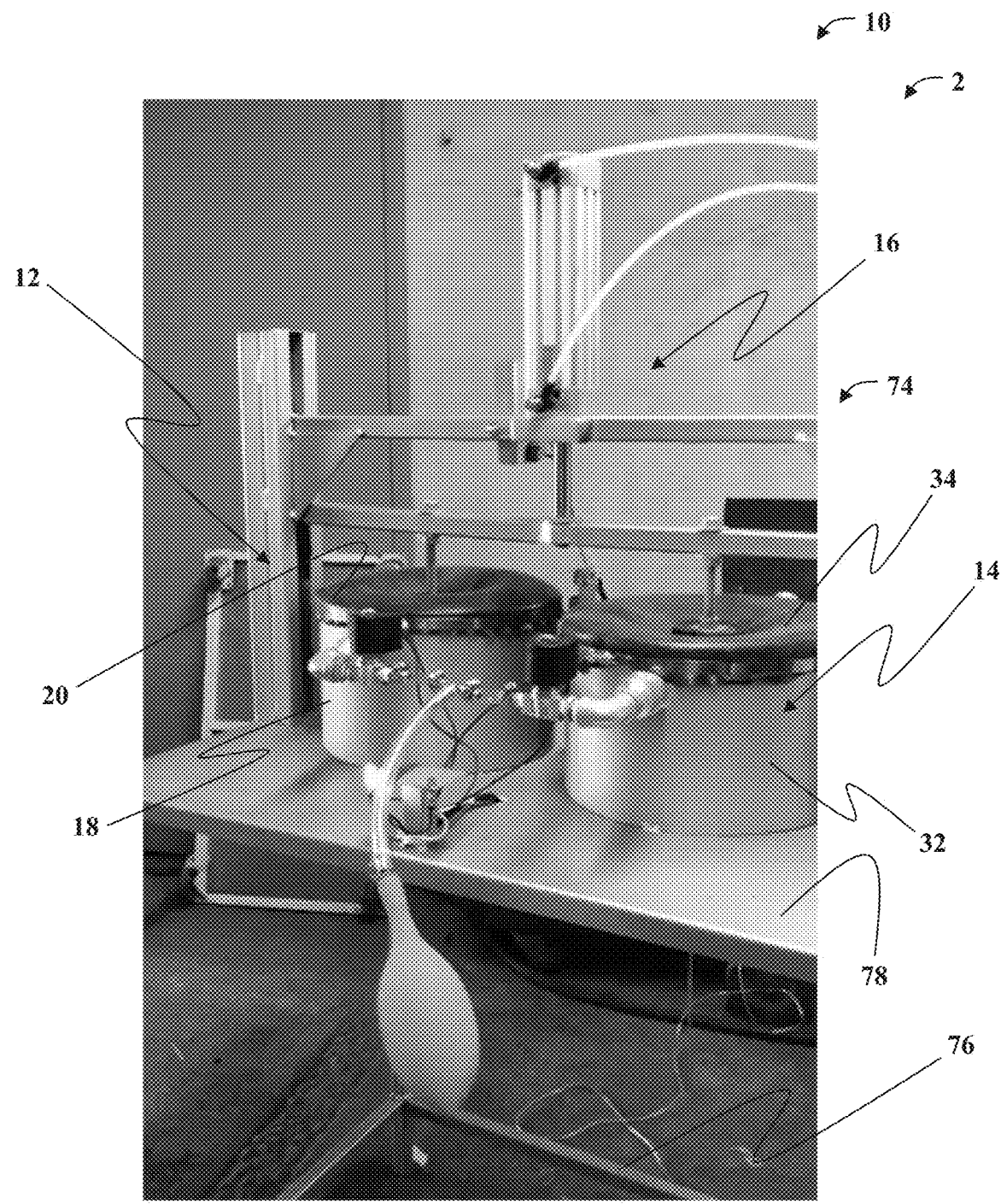
FIG. 3 is a perspective view of the respirator ventilator device, according to embodiments of the present invention.

With reference to the drawings and in operation, the present invention provides a respiratory ventilator device that includes a low-cost ventilator device for respiratory support for treatment of patients suffering from pneumonia and/or COVID-19, and non COVID-19 patients suffering from other respiratory diseases. The respiratory ventilator system 10 provides respiratory support that replicates the human breathing mechanism for patients that require it, because of illnesses such as pneumonia, COVID-19 related or not, at low cost and with ease of fabrication.

The present invention solves the cost problem of known ventilators by providing a respiratory ventilator system that can be easily made in a metal workshop without specialized or complex machinery, equipment, and tooling, making feasible its immediate production. Additional advantages of the present invention include a respiratory ventilator system that replicates the natural mechanism of human respiration for both inhalation and exhalation, making it safe and reliable.

Referring to FIGS. 1-18, in the illustrated embodiment, the present invention includes a respiratory ventilator device 2 including a respiratory ventilator system 10 that is coupled to a patient respiratory circuit 3 for providing air to a patient's lungs to facilitate breathing. The respiratory ventilator system 10 is mounted within a housing 4 and includes an inhaled air assembly 6, an exhaled air assembly 7, and a control system 8. The inhaled air assembly 6 is coupled to the patient respiratory circuit 3 and is configured to channel a volume of inhalation air to a patient's lungs via the patient respiratory circuit 3 to assist in patient inhalation. The volume of inhalation air may be drawn from ambient air and/or may be supplemented with oxygen. The exhaled air assembly 7 coupled to the patient respiratory circuit 3 and is configured to remove air from the patient's lungs via the patient respiratory circuit 3 to assist in a patient exhalation. The control system 8 is operatively coupled to the inhaled air assembly 6 and the exhaled air assembly 7 and configured to operate the respiratory ventilator device in an inhalation mode and an exhalation mode.

In some embodiments, the respiratory ventilator system 10 includes the inhaled air assembly 6 including an injector diaphragm assembly 12, the exhaled air assembly 7 including an extractor diaphragm assembly 14, and the control system 8 including a reciprocating assembly 16 coupled to the injector diaphragm assembly 12 and the extractor diaphragm assembly 14.

The injector diaphragm assembly 12 includes an injector diaphragm housing 18 and an air injection diaphragm 20 coupled to a top portion of the injector diaphragm housing 18. For example, the injector diaphragm housing 18 may include a cylindrical tank (or any other shaped tank such as conical, spherical, pyramidal, etc.) having an open top end. The air injection diaphragm 20 may include a flexible silicone rubber assembly (or any other suitable flexible material) that is attached to the open top end of the cylindrical tank of the injector diaphragm housing 18 to define an adjustable volume within the injector diaphragm housing 18. The injector diaphragm housing 18 includes an injector inlet port 22, an injector outlet port 24, an injector check valve assembly 26 coupled to the injector inlet port 22, and an injector solenoid valve assembly 28 coupled to the injector outlet port 24. The injector diaphragm housing 18 may also include an injector volume reduction member 30 positioned within an interior of the injector diaphragm housing 18 for reducing the internal volume of injector diaphragm housing 18. For example, the injector volume reduction member 30 may include a conic metal piece located inside the cylindrical tank of the injector diaphragm housing 18 for reducing the internal volume of injector cylindrical tank. The injector volume reduction member 30 may also have any suitable shape such as, for example, conical, spherical, pyramidal, etc., and be formed of any suitable material such as metal, plastic, or any other suitable material.

The extractor diaphragm assembly 14 includes an extractor diaphragm housing 32 and an air extraction diaphragm 34 coupled to a top portion of the extractor diaphragm housing 32. For example, the extractor diaphragm housing 32 may include a cylindrical tank (or any other shaped tank such as conical, spherical, pyramidal, etc.) having an open top end. The air extraction diaphragm 34 may include a flexible silicone rubber assembly (or any other suitable flexible material) that is attached to the open top end of the cylindrical tank of the extractor diaphragm housing 32 to define an adjustable volume within the extractor diaphragm housing 32. The air extraction diaphragm 34 is attached to the open top end of the cylindrical tank to define an adjustable volume within the extractor diaphragm housing 32. The extractor diaphragm housing 32 includes an extractor inlet port 36, an extractor outlet port 38, an extractor solenoid valve assembly 40 coupled to the extractor inlet port 36, and an extractor check valve assembly 42 coupled the extractor outlet port 38. The extractor diaphragm housing 32 may also include an extractor volume reduction member 44 positioned within an interior of the extractor diaphragm housing 32 for reducing the internal volume of extractor diaphragm housing 32. For example, the extractor volume reduction member 44 may include a conic metal piece located inside the cylindrical tank of the extractor diaphragm housing 32 for reducing the internal volume of extractor cylindrical tank. The extractor volume reduction member 44 may also have any suitable shape such as, for example, conical, spherical, pyramidal, etc., and be formed of any suitable material such as metal, plastic, or any other suitable material.

The reciprocating assembly 16 coupled to the injector diaphragm assembly 12 and the extractor diaphragm assembly 14 and is configured to operate the respiratory ventilator system 10 between an inhalation mode 46 during which air is injected into a patient's lungs, and an exhalation mode 48 during which air is extracted from the patient's lungs.

The reciprocating assembly 16 includes an air injection diaphragm pusher 50, an air extraction diaphragm pusher 52, a support bar 54 coupled to the air injection diaphragm pusher 50 and the air extraction diaphragm pusher 52, and a reciprocating motor assembly 56 coupled to the support bar 54. The reciprocating motor assembly 56 includes a cylinder rod 58 coupled to the support bar 54 and a motor 60 coupled to the cylinder rod 58 to cause the cylinder rod 58 and support bar 54 to move in a reciprocating motion. The motor 60 may include, for example, a pneumatic cylinder, and/or any other reciprocating mechanism suitable to implement a reciprocating motion.

The air injection diaphragm pusher 50 is coupled to the support bar 54 and the air injection diaphragm 20 such that movement of the support bar 54 causes movement of the air injection diaphragm 20. Similarly, the air extraction diaphragm pusher 52 is coupled to the support bar 54 and the air extraction diaphragm 34 such that movement of the support bar 54 causes movement of the air extraction diaphragm 34.

Figure 14:
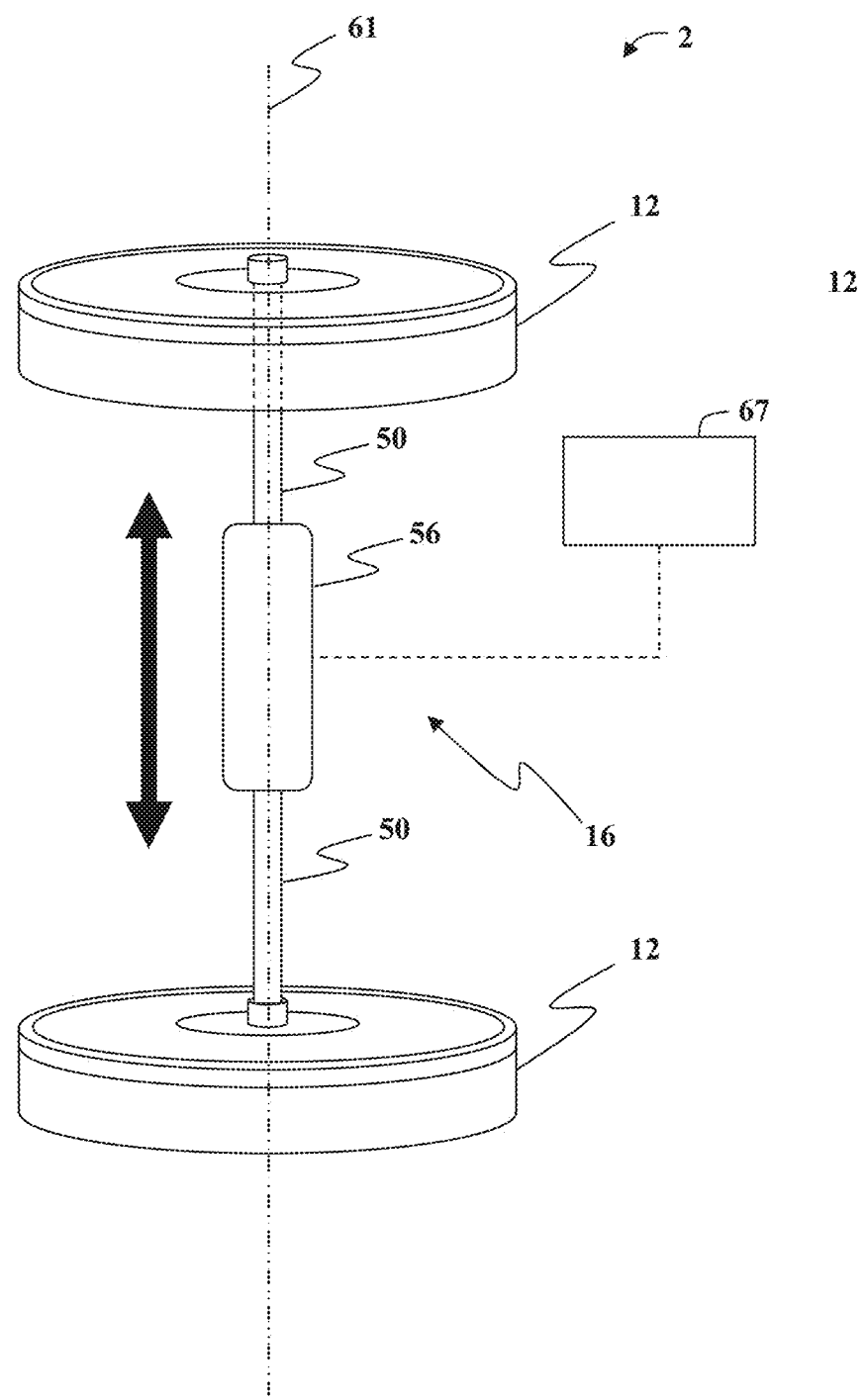
FIGS. 14 and 15 are schematic views of the respirator ventilator device.

In some embodiments, as shown in FIGS. 5-14, the injector diaphragm assembly 12 and the extractor diaphragm assembly 14 may be orientated along a centerline axis 61 with the air injection diaphragm pusher 50 coaxially aligned with the air extraction diaphragm pusher 52 along a centerline axis 61. In some embodiments, the injector diaphragm assembly 12 and the extractor diaphragm assembly 14 may be orientated in a vertically stacked arrangement as shown in FIG. 14. In other embodiments, the injector diaphragm assembly 12 and the extractor diaphragm assembly 14 may be orientated in a horizontal arrangement.

In some embodiments, an inlet air supply connector assembly 62 may be coupled to the air injector inlet port 22 for providing a supply of air to the injector diaphragm assembly 12. In other embodiments, the injector inlet port 22 may be configured to channel ambient air to the injector diaphragm assembly 12. In addition, in some embodiments, an exhaust air outlet connector assembly 64 may be coupled to the extractor outlet port 38 for receiving and/or collecting a volume of air being exhausted from the extractor diaphragm assembly 14. For example, the exhaust air outlet connector assembly 64 may include an air filtration system for filtering the air exhausted from the extractor diaphragm assembly 14. A patient respiratory circuit 3 is coupled to the injector outlet port 24 and the extractor inlet port 36 for channeling air from the injector diaphragm assembly 12 to the patient's lungs and for channeling air from the patient's lungs to the extractor diaphragm assembly 14.

The respiratory ventilator system 10 also includes the control system 8 including a controller 67 for operating the respiratory ventilator system 10. The controller 67 is operatively coupled to a micro switch assembly 68 that is coupled to the solenoid valve assemblies 28, 40 and the reciprocating motor assembly 56. The micro switch assembly 68 includes a micro switch 70 and a vertically adjustable micro switch support 72 coupled to the micro switch 70 for adjusting a vertical position of the micro switch 70. For example, in the illustrated embodiment, the micro switch 70 is positioned to allow the support bar 54 to periodically contact the micro switch 70 as the support bar 54 is moved through a reciprocating motion. The function of the micro switch assembly 68 may also be performed by other type of switches such as magnetic or proximity switches.

The respiratory ventilator system 10 may also include the housing 4 including a support assembly 74 for supporting the injector diaphragm assembly 12, an extractor diaphragm assembly 14, and/or the reciprocating assembly 16 from a ground surface. The support assembly 74 may include a base frame 76 mounted on the ground surface, a support plate 78 coupled to the base frame 76, and a cylinder support frame 80 mounted to the support plate 78 and/or the base frame 76. The cylinder support frame 80 is coupled to the reciprocating assembly 16 for supporting the reciprocating assembly 16 from the support plate 78 and/or the base frame 76. The injector diaphragm assembly 12 and the extractor diaphragm assembly 14 may each be mounted onto the support plate 78 to support the injector diaphragm assembly 12 and the extractor diaphragm assembly 14 from the base frame 76. The vertically adjustable micro switch support 72 is mounted onto the support plate 78 and positioned to allow the support bar 54 to periodically contact the micro switch 70 as the support bar 54 is moved through a reciprocating motion.

The components of the respiratory ventilator system 10 may be built with materials suitable for sanitary and medical purposes, such as stainless steel, including pneumatic fittings. The support structure of the device (support assembly, frame, base, etc.) can be built of carbon steel with a suitable finish such as powder coat paint. The diaphragms 20, 34 may be made, for example, with silicone rubber.

During operation, the respiratory ventilator system 10 operates to cyclically inject fresh air to the patient lungs and alternatively extracting spent air from patient lungs, using fittings and tubing commonly used in hospital patient respiratory circuits, that can be connected to the respiratory ventilator system 10.

For example, during the inhalation mode 46, at cycle's beginning diaphragms 20, 34 are in a first position 100. The pneumatic cylinder 60, which is attached firmly to frame 74, pushes down the support bar 54 and cylinder rod 58, which in-turn, causes the diaphragm pushers 50, 52 to push downwards onto the air injection diaphragm 20 and the air extraction diaphragm 34 to reduce the internal volumes of the injector diaphragm housing 18 and the extractor diaphragm housing 32, respectively, and forcing air out of the respiratory ventilator system 10.

During the inhalation mode 46, air contained within the injector diaphragm assembly 12 flows through the injector solenoid valve assembly 28 (which may also be replaced by a check valve) to the patient respiratory circuit 3, which with appropriate tubing and fittings, will be injected into patient's lungs. At the same time, the extractor diaphragm assembly 14 pushes spent air, previously extracted from the patient's lungs in a previous cycle, out through extractor check valve assembly 42 to the exhaust air outlet connector assembly 64. This spent air can be filtered and or sterilized downstream in a suitable machine for that purpose to render it harmless.

When the cylinder rod 58 of the pneumatic cylinder 60 reaches a bottom position 102, the respiratory ventilator system 10 transitions to operate in the exhalation mode 48. For example, as the cylinder rod 58 reaches the bottom position 102, the support bar 54 activates the micro switch 70, which reverses the direction of the pneumatic cylinder movement, causing the cylinder rod 58, support bar 54, diaphragm pushers 50, 52, and the air injection diaphragm 20 and the air extraction diaphragm 34 to move upwards.

As the air injection diaphragm 20 moves in an upward direction, the injector diaphragm assembly 12 draws in fresh air from the inlet air supply connector assembly 62 through the injector check valve assembly 26. Simultaneously, as the air extraction diaphragm 34 moves in the upward direction, the extractor diaphragm assembly 14 will suction spent air from patient's lungs through extractor solenoid valve assembly 40.

Fresh air can be treated upstream prior to entering injector check valve assembly 26 with suitable devices and/or machines and connections for filtering, humidifying, oxygenating, etc. When the pneumatic cylinder 60 reaches the top position 100, the cycle repeats itself, injecting fresh air and alternatively extracting spent air from patient lungs.

Device air volume displaced per cycle may be adjusted either by reducing the distance separating bar 54 from diaphragms 20, 34 at the pushers 50, 52 and/or adjusting the height of micro switch assembly 68 which will reduce the length of the cylinder stroke, and consequently the volume displaced in each cycle.

Cycle time can be modified to desired frequency per minute (respiratory rate) manually by adjusting the cylinder exhaust valves and cylinder pressure, or by installing an electronic/electric timer on the machine, or by means of a computer controlled proportional flow valve.

As was mentioned above, in either fresh air suction through injector check valve assembly 26 and or spent air expulsion through extractor check valve assembly 42 required accessories such as UV air sterilizers, humidifiers, heaters, filters, can be installed.

In the illustrated embodiment, the inhaled air assembly 6 is coupled to the patient respiratory circuit 3 and is configured to channel a volume of inhalation air to a patient's lungs via the patient respiratory circuit 3 to assist in patient inhalation. The exhaled air assembly 7 is coupled to the patient respiratory circuit 3 and is configured to remove air from the patient's lungs via the patient respiratory circuit 3 to assist in a patient exhalation. In some embodiments, the patient respiratory circuit 3 may include a patient face mask 110, a y-junction assembly 112 coupled to a ventilator pressure and flow sensor 113 and to the face mask 110 or to an endotracheal tubing, an inspiratory tubing 114, and an expiratory tubing 116. The inspiratory tubing 114 is coupled between the inhaled air assembly 6 and the y-junction assembly 112 to provide air to the face mask 110 or endotracheal tubing. The expiratory tubing 116 is coupled between the y-junction assembly 112 and the exhaled air assembly 7 for channeling exhaled air from the face mask 110 to the exhaled air assembly 7. In some embodiments, the patient respiratory circuit 3 may include a humidifier assembly 118 coupled to the inhaled air assembly 6 and the inspiratory tubing 114 for regulating the humidity of the inhalation air.

The control system 8 is operatively coupled to the inhaled air assembly 6 and the exhaled air assembly 7 and is configured to operate the respiratory ventilator device 2 in an inhalation mode 46 and an exhalation mode 48. The control system 8 operates the inhaled air assembly 6 to generate a positive air pressure to channel the volume of inhalation air to the patient's lungs during the inhalation mode 46 and operates the exhaled air assembly 7 to generate a negative air pressure to remove the air from the patient's lungs during the exhalation mode 48.

Figure 15:
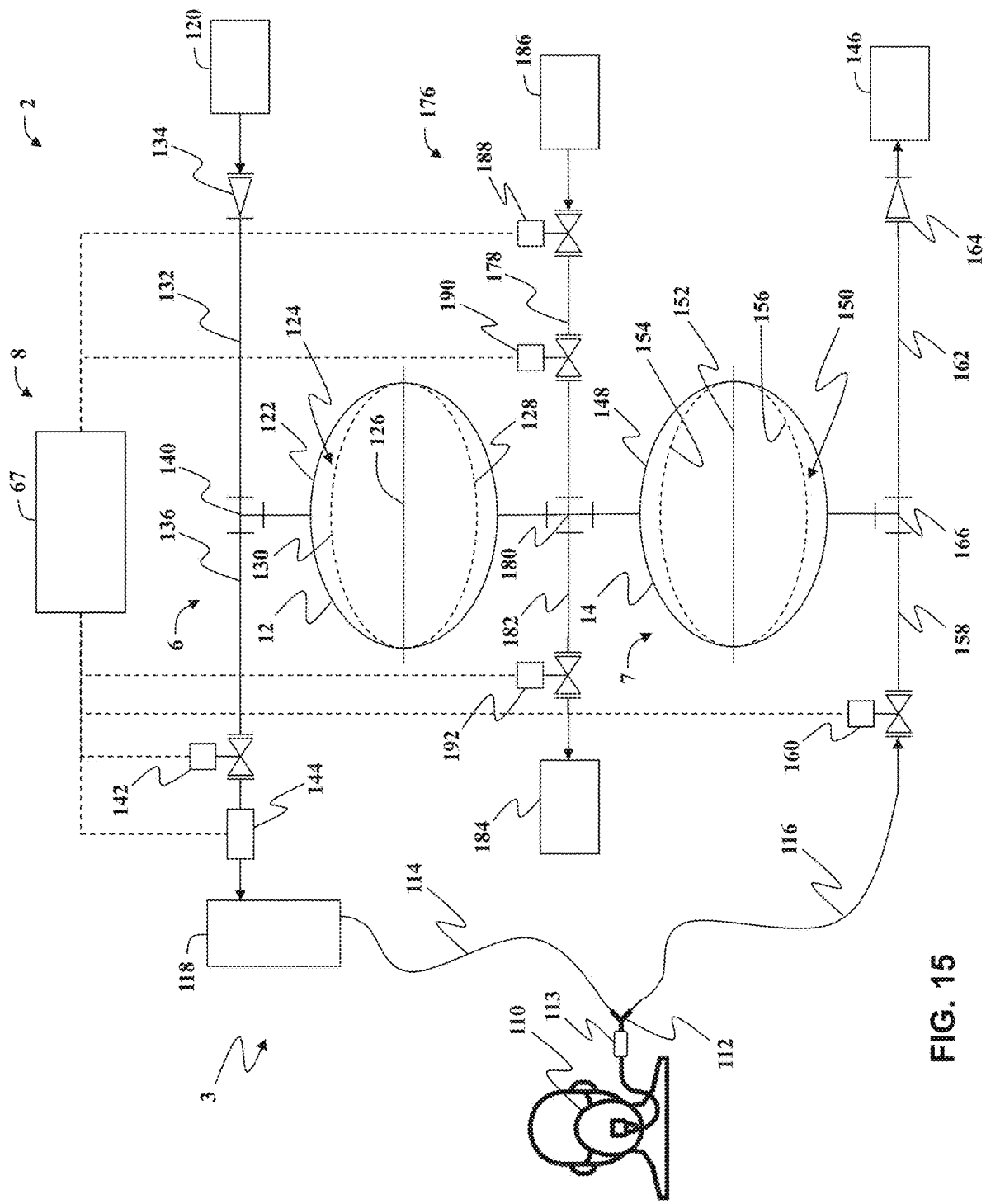
Figure 16:
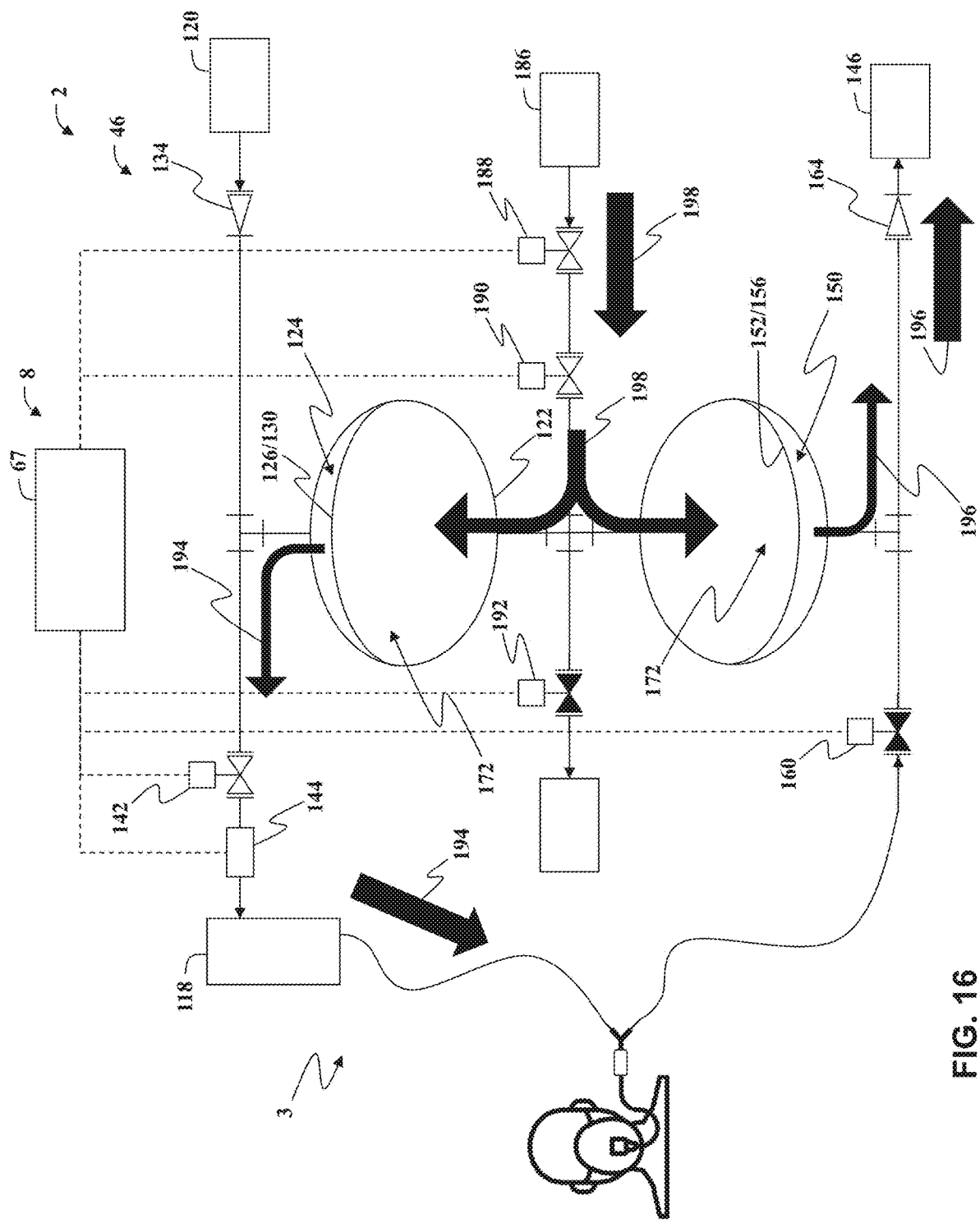
FIG. 16 is a schematic view of the respirator ventilator device operating in an inhalation mode.

Referring to FIG. 15, in some embodiments, the inhaled air assembly 6 includes an injector diaphragm assembly 12 that is coupled between the patient respiratory circuit 3 and a supply of inhalation air 120 for receiving the volume of inhalation air from the supply of inhalation air 120 and delivering the volume of inhalation air to the patient respiratory circuit 3. The injector diaphragm assembly 12 includes an injector diaphragm housing 122 that includes an inner surface defining an inhalation air chamber 124 and an inhalation diaphragm 126 that is coupled to the injector diaphragm housing 122 to enclose the inhalation air chamber 124. The inhalation diaphragm 126 is moveable between a first inhalation position 128 and a second inhalation position 130 to adjust a volume of the inhalation air chamber 124. The inhalation air chamber 124 defines a first volume of the inhalation air chamber 124 with the inhalation diaphragm 126 in the first inhalation position 128 (shown in FIG. 17) and defines a second volume of the inhalation air chamber 124 with the inhalation diaphragm 126 in the second inhalation position 130 (shown in FIG. 16). The first volume of the inhalation air chamber 124 is greater than the second volume of the inhalation air chamber 124.

The injector diaphragm assembly 12 also includes an inhalation inlet line 132 that is coupled to the injector diaphragm housing 122 and is configured to receive the volume of inhalation air from the supply of inhalation air 120 into the injector diaphragm housing 122. An inhalation check valve assembly 134 is coupled to the inhalation inlet line 132 and is positioned between the supply of inhalation air 120 and the injector diaphragm housing 122. An inhalation outlet line 136 is coupled to the injector diaphragm housing 122 and is configured to deliver the volume of inhalation air to the patient respiratory circuit 3 from the injector diaphragm housing 122. An inhalation tee fitting 140 is coupled between the inhalation inlet line 132, the inhalation outlet line 136, and the injector diaphragm housing 122 such that the inhalation inlet line 132, the inhalation outlet line 136, and the injector diaphragm housing 122 are in fluid communication.

An inhalation solenoid valve (or check valve) assembly 142 is coupled to the inhalation outlet line 136 and positioned between injector diaphragm housing 122 and the patient respiratory circuit 3 to selectively channel fresh air (oxygenated or not) from the injector diaphragm housing 122 to the patient respiratory circuit 3. A sensor assembly 144 may be coupled between the inhalation solenoid valve assembly 142 and the patient respiratory circuit 3 for sensing an air pressure, air flow, and/or oxygen % content being delivered to patient respiratory circuit 3. A sensor assembly may also be installed between y-junction and face mask or endotracheal tubing, which has the additional advantage of taking measurements closer to the patient.

The exhaled air assembly 7 includes an extractor diaphragm assembly 14 that is coupled between the patient respiratory circuit 3 and an exhaust air collection system 146 for receiving a volume of exhaled air from the patient respiratory circuit 3 and delivering the volume of exhaled air to the exhaust air collection system 146. In some embodiments, the exhaust air collection system 146 may include an air filtration system. The extractor diaphragm assembly 14 includes an extractor diaphragm housing 148 that includes an inner surface defining an exhalation air chamber 150. An exhalation diaphragm 152 is coupled to the extractor diaphragm housing 148 to enclose the exhalation air chamber 150. The exhalation diaphragm 152 is moveable between a first exhalation position 154 and a second exhalation position 156 to adjust a volume of the exhalation air chamber. The exhalation air chamber 150 defines a first volume of the exhalation air chamber 150 with the exhalation diaphragm 152 in the first exhalation position 154 and defines a second volume of the exhalation air chamber 150 with the exhalation diaphragm 152 in the second exhalation position 156. The first volume of the exhalation air chamber 150 is greater than the second volume of the exhalation air chamber 150.

The exhaled air assembly 7 also includes exhalation inlet line 158, an exhalation solenoid valve assembly 160, an exhalation outlet line 162, and an exhalation check valve assembly 164. The exhalation inlet line 158 is coupled to the extractor diaphragm housing 148 and is configured to receive the volume of exhaled air from the patient respiratory circuit 3 into the extractor diaphragm housing 148. The exhalation solenoid valve assembly 160 is coupled to the exhalation inlet line 158 and is configured to selectively channel exhaled air from the patient respiratory circuit 3 into the extractor diaphragm housing 148. The exhalation outlet line 162 is coupled to the extractor diaphragm housing 148 and is configured to deliver the volume of exhaled air to the exhaust air collection system 146. The exhalation check valve assembly 164 is coupled between the exhalation outlet line 162 and the exhaust air collection system 146. An exhalation tee fitting 166 is coupled between the exhalation inlet line 158, the exhalation outlet line 162, and the extractor diaphragm housing 148 such that the exhalation inlet line 158, the exhalation outlet line 162, and the extractor diaphragm housing 148 are in fluid communication.

In the illustrated embodiment, the control system 8 includes a controller 67 that includes a processor that is coupled to a memory device that stores an operating program that includes computer executable instructions that, when executed by the processor, cause the processor to operate the respiratory ventilator system 10 in the inhalation mode 46 and the exhalation mode 48. In some embodiments, the control system 8 may also include a display assembly 168 that is mounted to the housing 4 and coupled to the processor. The processor is programmed to display computer generated graphic user interface on the display assembly 168 to enable a user to operate the respiratory ventilator system 10 and/or display various status icons and messages related to the operation of the respiratory ventilator system 10. The control system 8 may also include a control panel 170 having one or more input buttons that enables the user to operate the respiratory ventilator system 10.

Figure 4A:
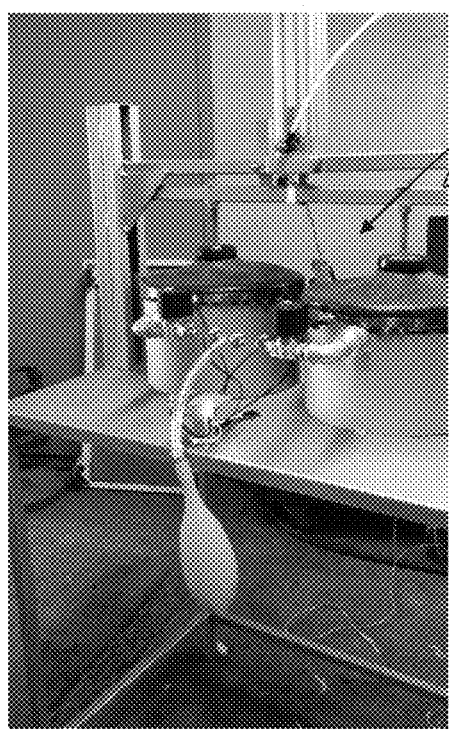
FIGS. 4A-4D are perspective views of the respirator ventilator device during operation.
Figure 4B:
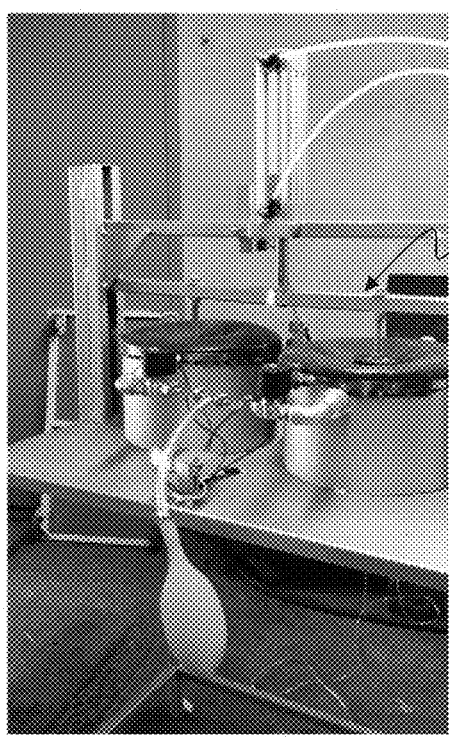
Figure 4C:
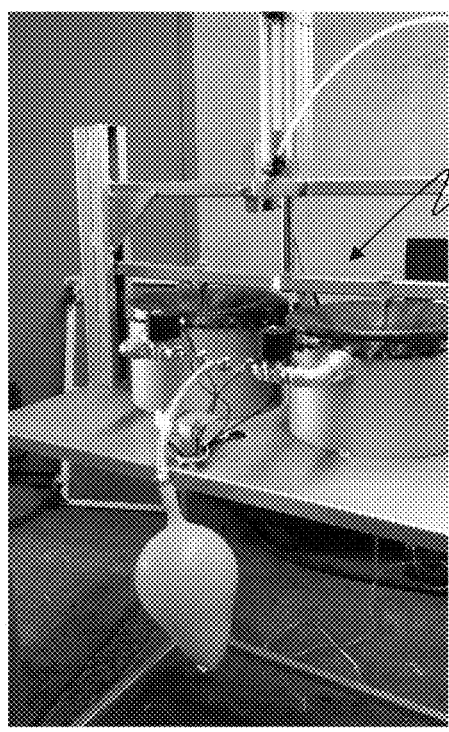
Figure 4D:
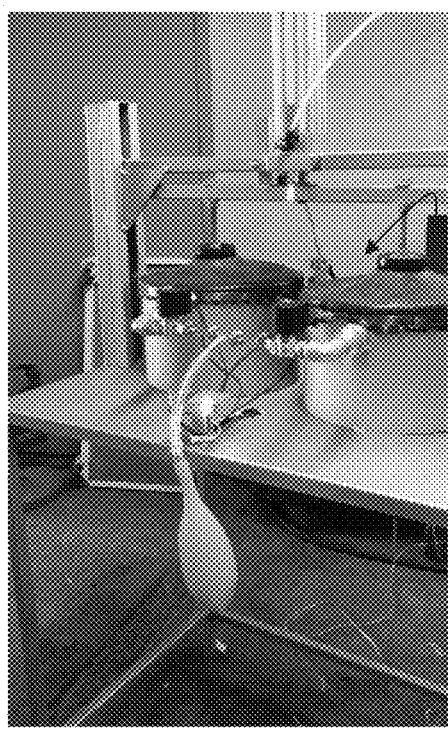
Figure 5:
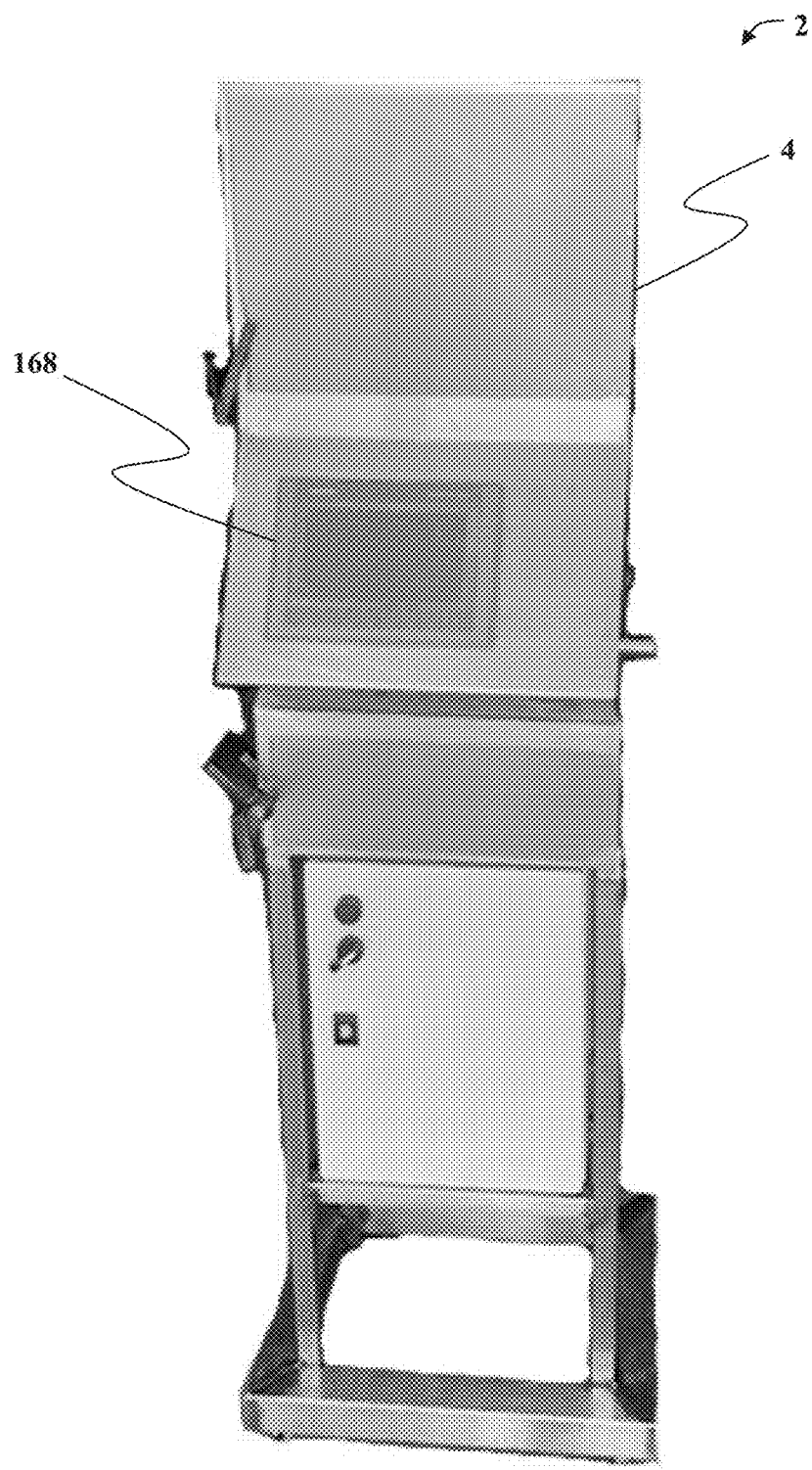
FIGS. 5-13 are perspective views of the respirator ventilator device, according to embodiments of the present invention.
Figure 6:
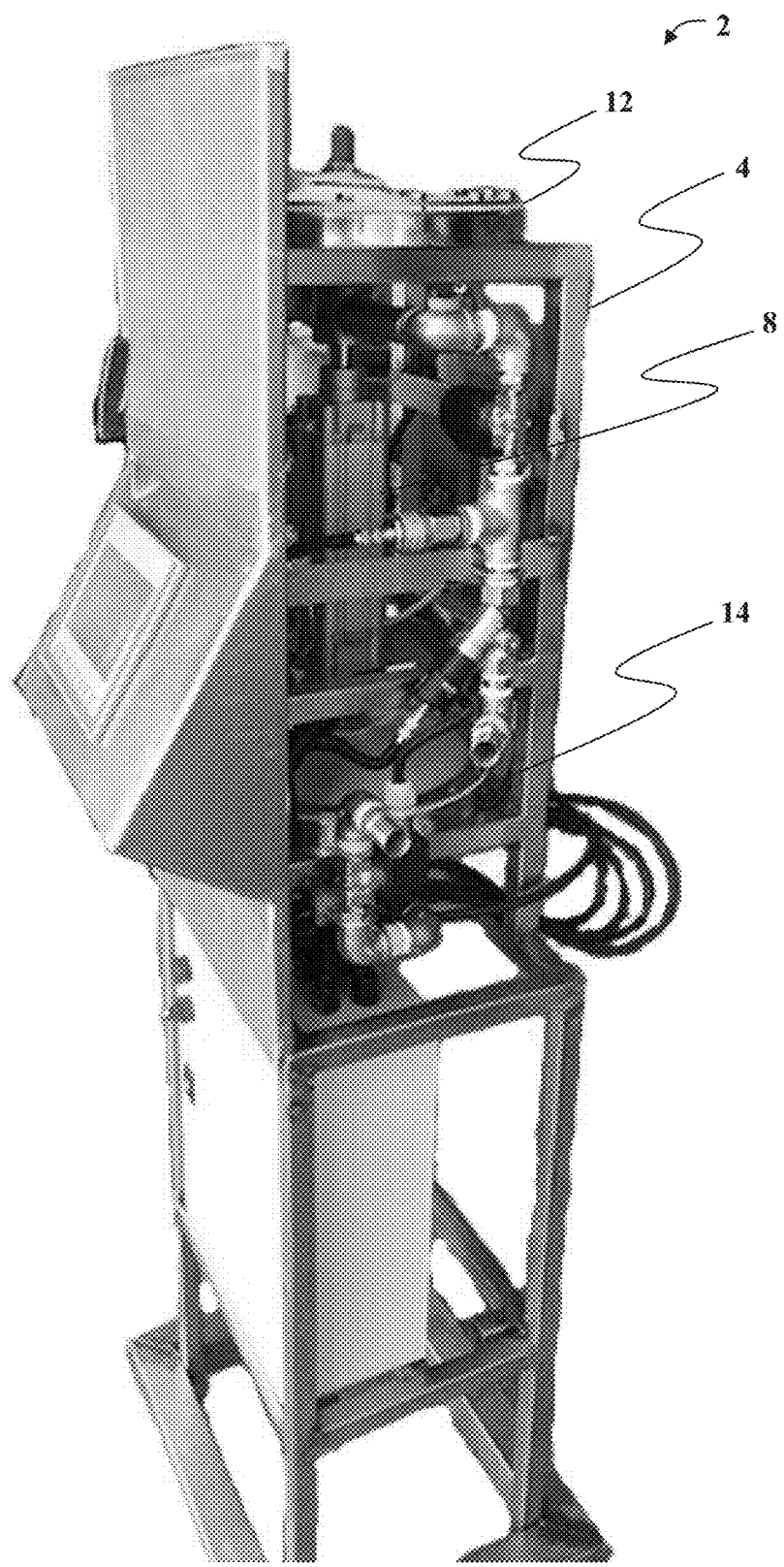
Figure 7:
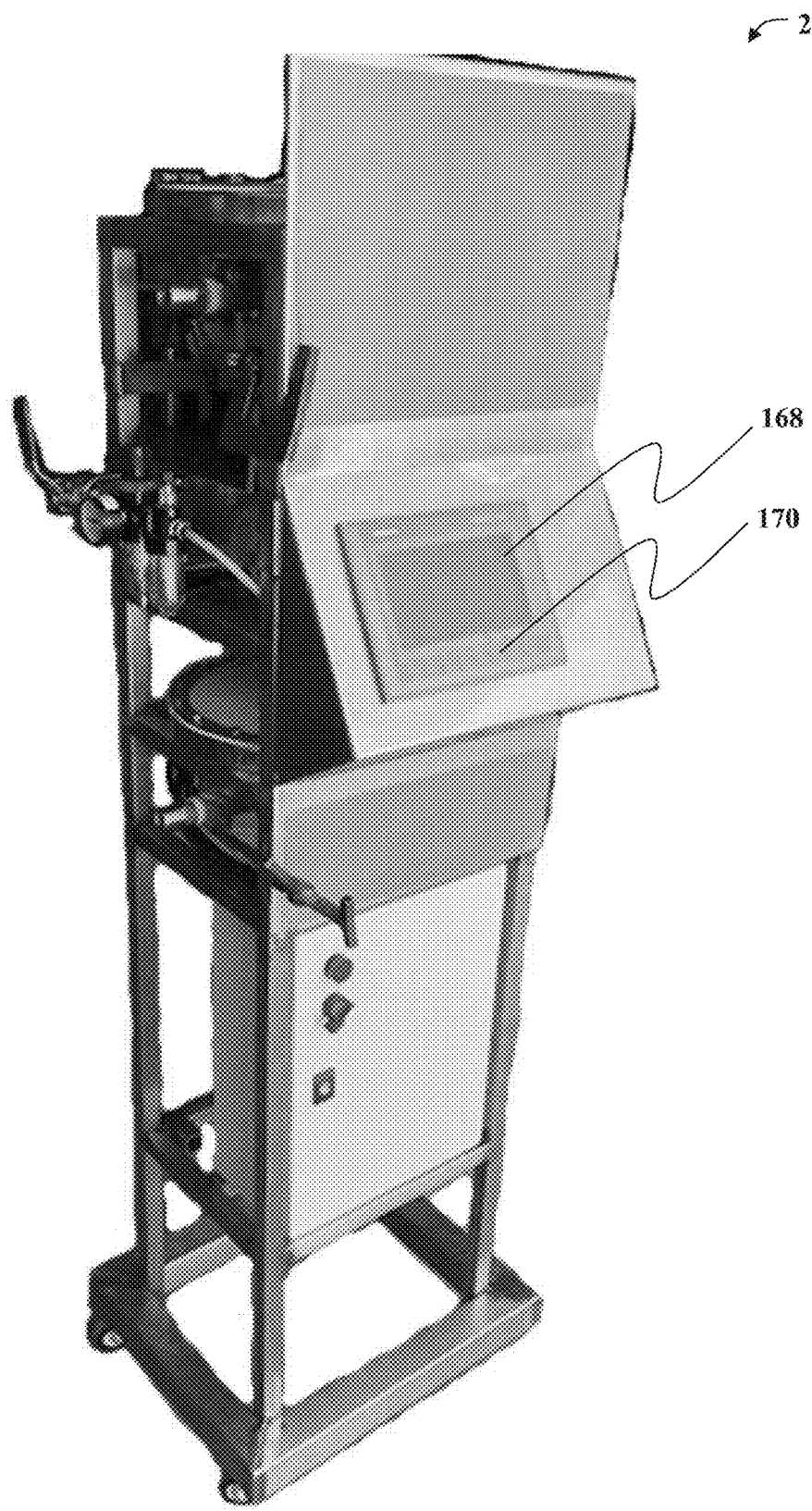
Figure 8:
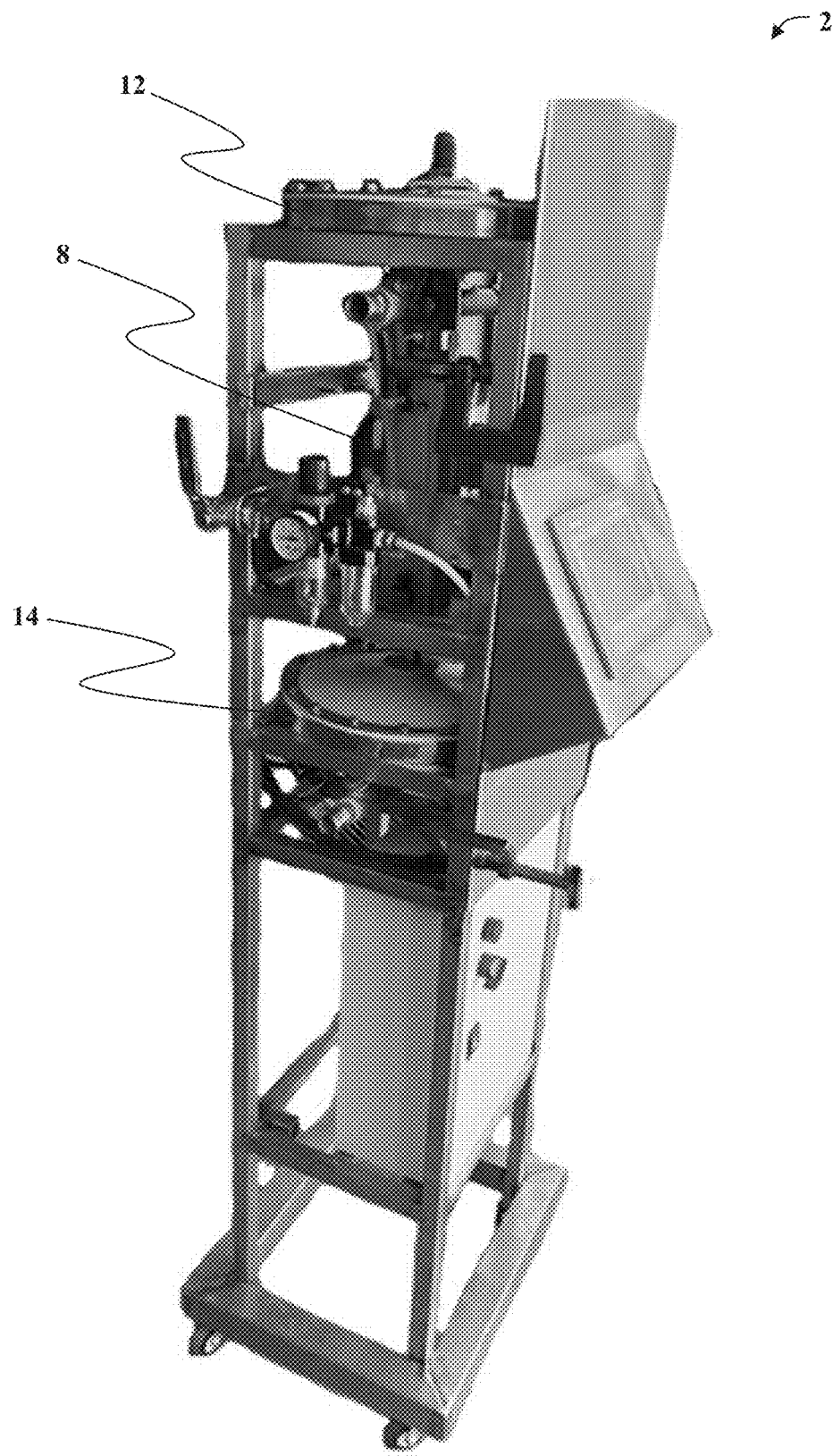
Figure 9:
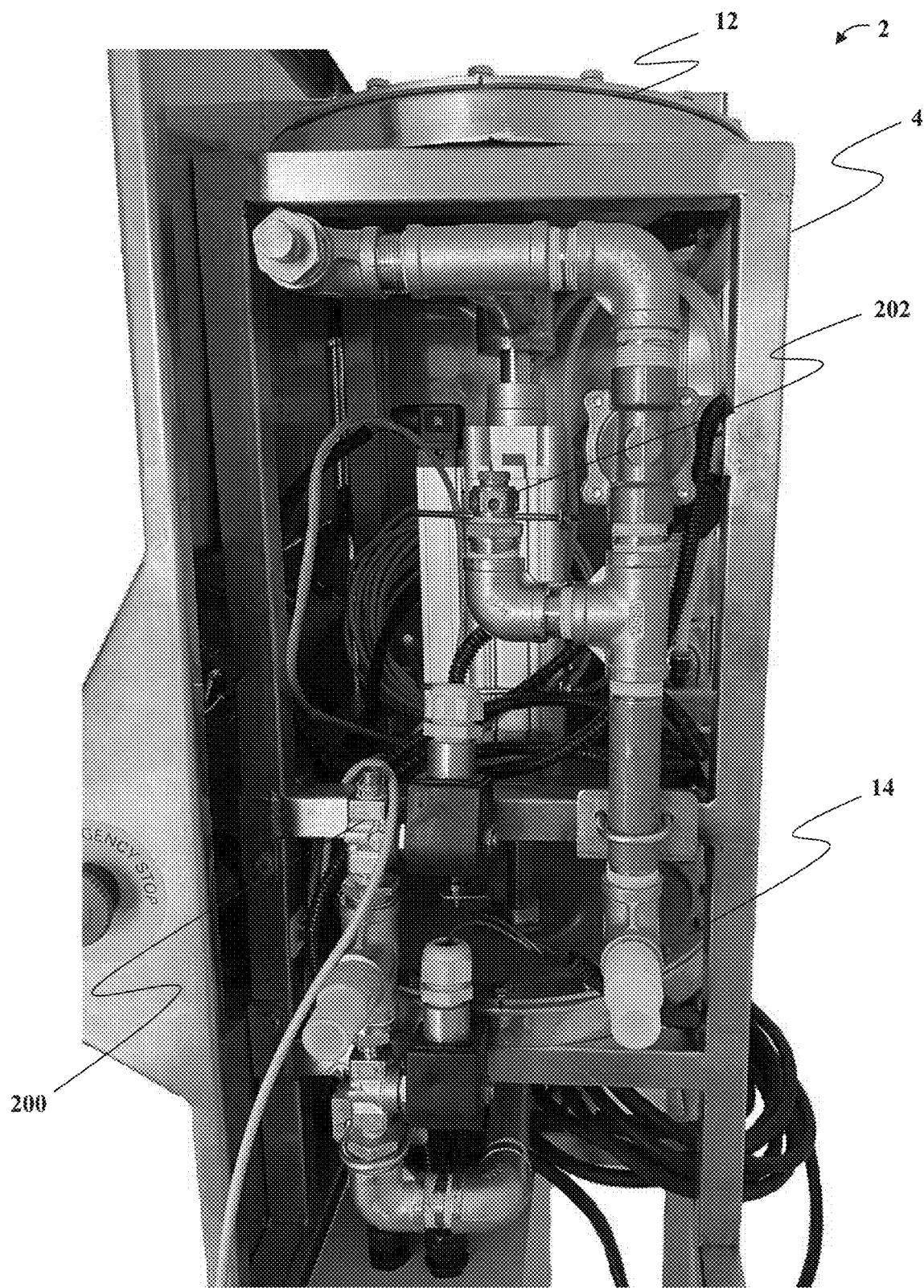
Figure 10:
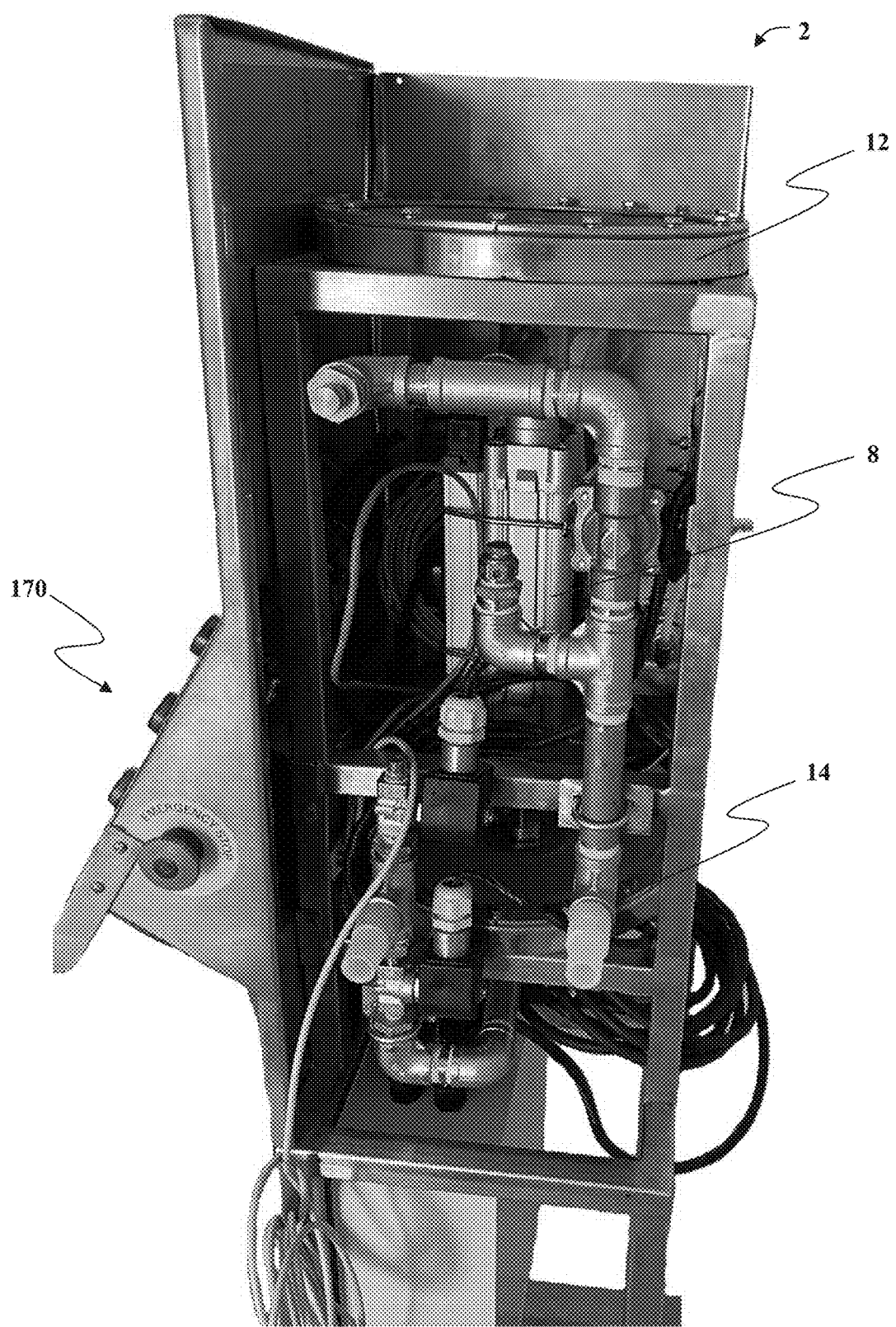
Figure 11:
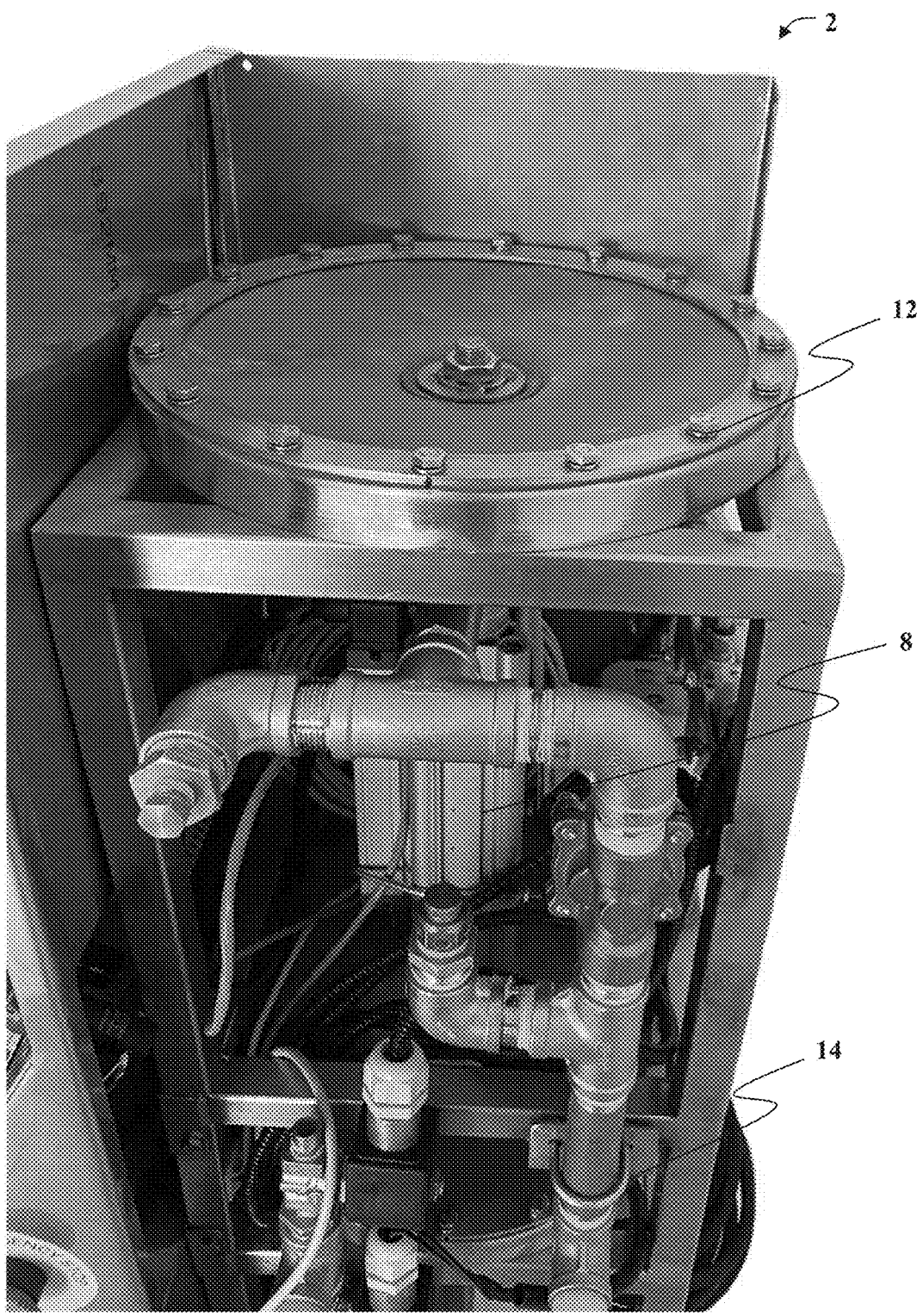
Figure 12:
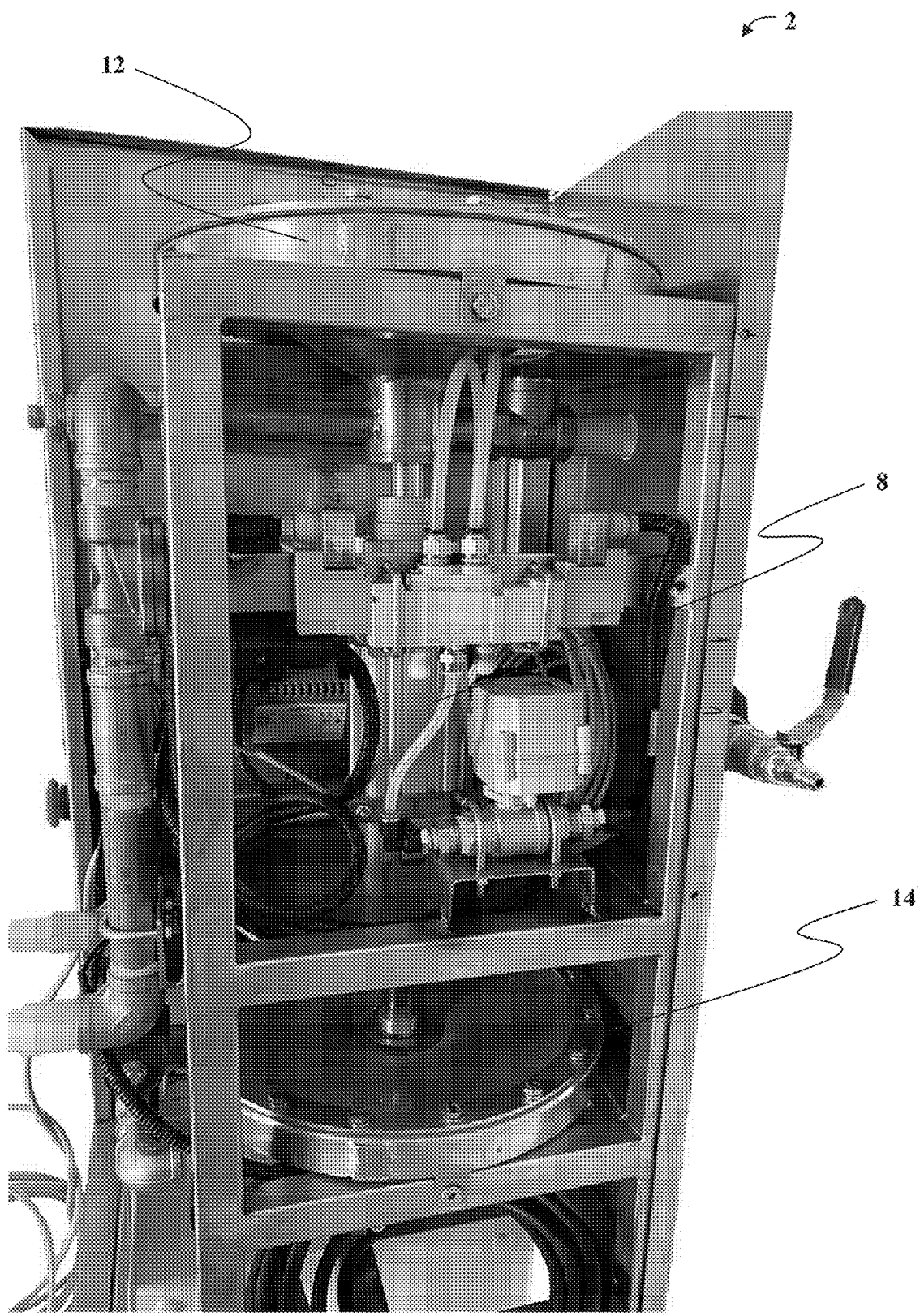
Figure 13:
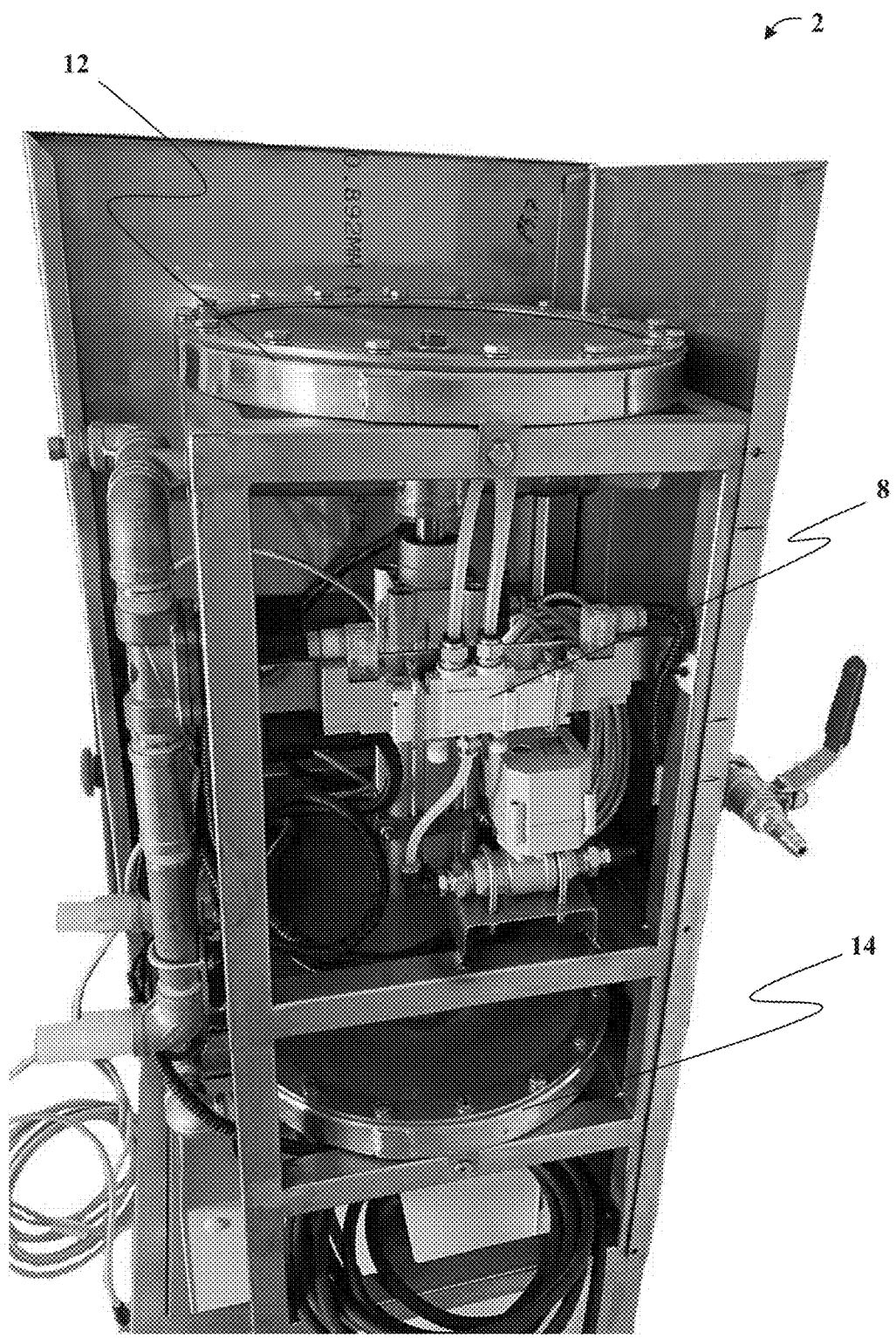
Figure 17:
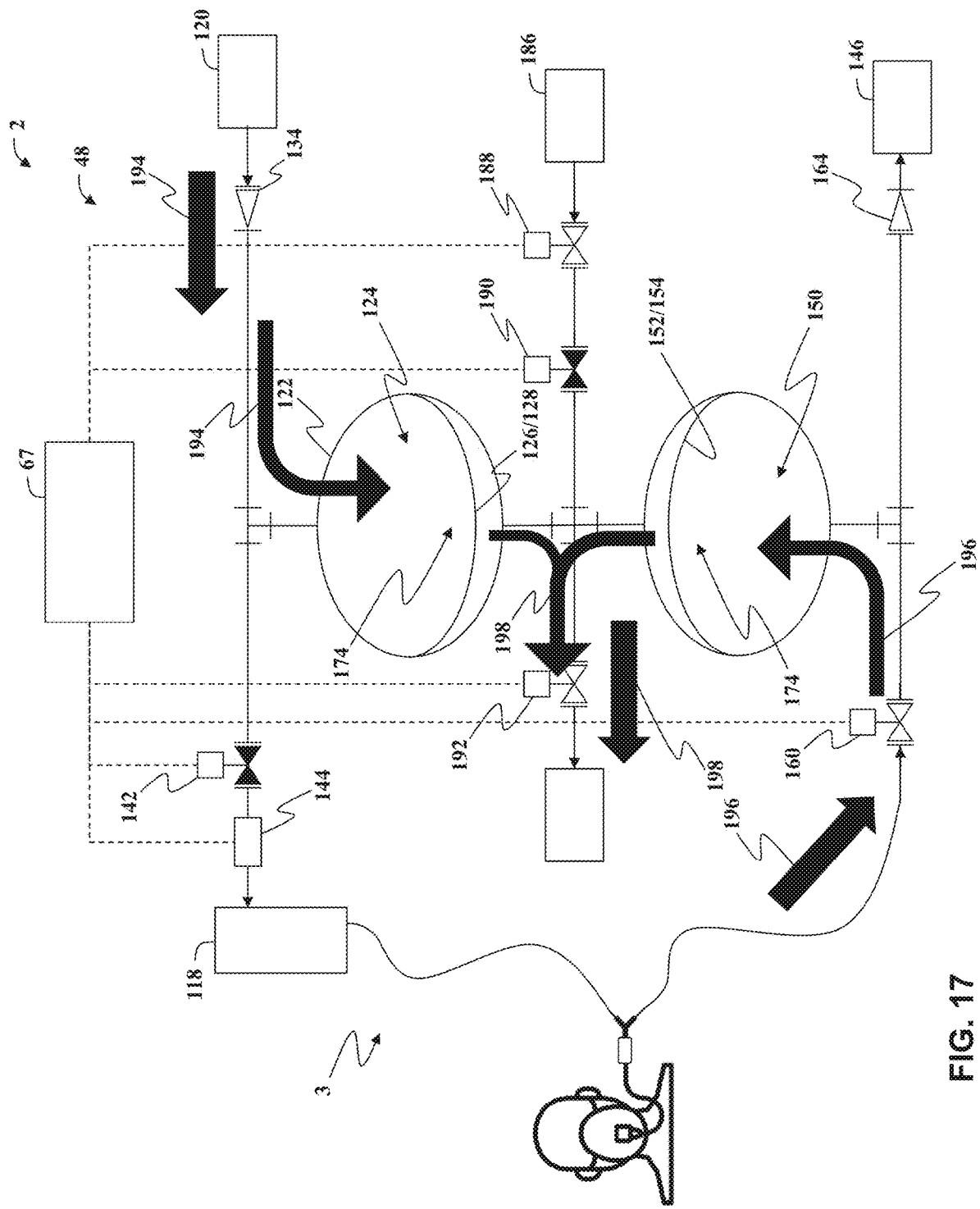
FIG. 17 is a schematic view of the respirator ventilator device operating in an exhalation mode.
Figure 18:
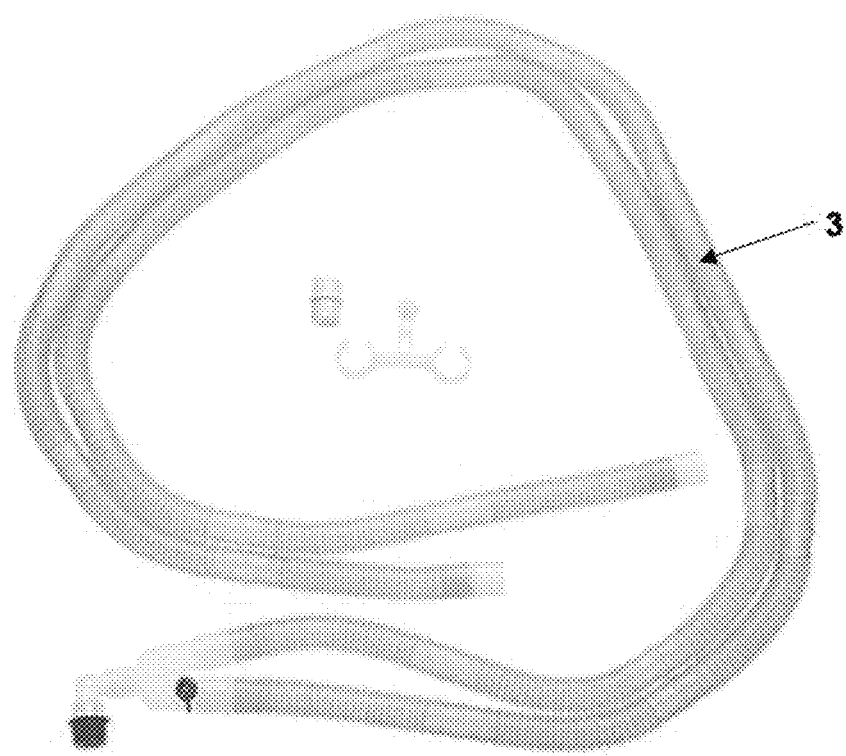
FIG. 18 is a partial perspective view of a patient respiratory circuit that may be used with the respirator ventilator device.

The control system 8 is configured to operate the inhaled air assembly 6 and the exhaled air assembly 7 in an operating cycle that includes a compression phase 172 (shown in FIGS. 4B and 16) and an expansion phase 174 (shown in FIGS. 4D and 17).

The control system 8 is configured to operate the inhaled air assembly 6 in the compression phase 172 to move the inhalation diaphragm 126 from the first inhalation position 128 to the second inhalation position 130 to reduce the volume of the inhalation air chamber 124 to deliver the volume of inhalation air to the patient respiratory circuit 3. In the compression phase 172, the control system 8 simultaneously operates the exhaled air assembly 7 to move the exhalation diaphragm 152 from the first exhalation position 154 to the second exhalation position 156 to reduce the volume of the exhalation air chamber 150 and deliver the volume of exhaled air to the exhaust air collection system 146.

The control system 8 is also configured to operate the inhaled air assembly 6 in the expansion phase 174 to move the inhalation diaphragm 126 from the second inhalation position 130 to the first inhalation position 128 to increase the volume of the inhalation air chamber 124 to receive the volume of inhalation air from the supply of inhalation air 120. The control system 8 also simultaneously operates the exhaled air assembly 7 in the expansion phase 174 to move the exhalation diaphragm 152 from the second exhalation position 156 to the first exhalation position 154 to increase the volume of the exhalation air chamber 150 to remove the air from the patient's lungs.

In some embodiments, the control system 8 includes the reciprocating assembly 16 coupled to the inhaled air assembly 6 and the exhaled air assembly 7 for operating the inhaled air assembly 6 and the exhaled air assembly 7 through the compression phase 172 and the expansion phase 174.

Referring to FIG. 15, in some embodiments, the control system 8 includes a pneumatic compressed air assembly 176 that is coupled to the inhaled air assembly 6 and the exhaled air assembly 7 for operating the inhaled air assembly 6 and the exhaled air assembly 7 through the compression phase 172 and the expansion phase 174. The pneumatic compressed air assembly 176 includes a compressed air inlet line 178 that is coupled to the inhaled air assembly 6 for channeling compressed air to the inhaled air assembly 6 to move the inhalation diaphragm 126 between the first and second inhalation positions 128, 130. The compressed air inlet line 178 is also coupled to the exhaled air assembly 7 for channeling compressed air to the exhaled air assembly 7 to move the exhalation diaphragm 152 between the first and second exhalation positions 154, 156. The pneumatic compressed air assembly 176 includes a cross fitting 180 coupled to the compressed air inlet line 178 and to the inhaled and exhaled air assemblies 6, 7 for channeling compressed air to the inhaled and exhaled air assemblies 6, 7. The pneumatic compressed air assembly 176 may also include a compressed air outlet line 182 coupled between the cross fitting 180 and a compressed air outlet 184 for channeling compressed air from the inhaled and exhaled air assemblies 6, 7. The pneumatic compressed air assembly 176 also includes the compressed air inlet line 178 coupled to a source of compressed air 186, a proportional solenoid valve 188 that is coupled to the compressed air inlet line 178, an inlet solenoid valve 190 that is coupled between the proportional solenoid valve 188 and the cross fitting 180, and outlet solenoid valve 192 that is coupled between the cross fitting 180 and the compressed air outlet 184.

During the inhalation mode 46, the control system 8 operates the inhaled air assembly 6 and the exhaled air assembly 7 in the compression phase 172 to operate the inhaled air assembly 6 to generate a positive air pressure to channel the volume of inhalation air 194 from the injector diaphragm assembly 12 to the patient's lungs and operate the exhaled air assembly 7 to channel the exhaled air 196 stored in the extractor diaphragm assembly 14 to the exhaust air collection system 146. In the compression phase 172, the control system 8 operates the pneumatic compressed air assembly 176 with the proportional solenoid valve 188 and the inlet solenoid valve 190 in an open position to channel compressed air 198 to the inhaled and exhaled air assemblies 6, 7, and with the outlet solenoid valve 192 operated in a closed position to prevent compressed air being channeled through the compressed air outlet 184. The control system 8 also operates the inhalation solenoid valve assembly 142 in an open position to channel oxygenated air from the injector diaphragm housing 122 to the patient respiratory circuit 3, and operates the exhalation solenoid valve assembly 160 in a closed position to prevent air from entering the exhaled air assembly 7.

During the exhalation mode 48, the control system 8 operates the inhaled air assembly 6 and the exhaled air assembly 7 in the expansion phase 174 to operate the exhaled air assembly 7 to generate a negative air pressure to remove exhaled air 196 from the patient's lungs and into the extractor diaphragm assembly 14 and operate the inhaled air assembly 6 to receive the volume of inhalation air 194 from the supply of inhalation air 120 through inhalation check valve assembly 134 and into the injector diaphragm assembly 12.

In the expansion phase 174, the control system 8 operates the pneumatic compressed air assembly 176 with the inlet solenoid valve 190 in a closed or partially closed position to limit compressed air channeled into the inhaled and exhaled air assemblies 6, 7, and with the outlet solenoid valve 192 operated in an open position to channel compressed air from the inhaled and exhaled air assemblies 6, 7 to the compressed air outlet 184. The control system 8 also operates the inhalation solenoid valve assembly 142 in a closed position to limit oxygenated air from being channeled to the patient respiratory circuit 3, and operates the exhalation solenoid valve assembly 160 in an open position to generate a negative air pressure to remove exhaled air 196 from the patient's lungs and into the extractor diaphragm assembly 14.

The respiratory ventilator device 2 provides a low cost ventilator device for respiratory support for Pneumonia, COVID-19, and non-COVID-19 patients with the purpose of the device to give respiratory support for patients in ICU. The medical parameters can be configured and controlled with the control system through standard electric/electronic equipment, such as PLC's, relay's, counters, timers, etc.

During the inhalation mode 46, compressed air is supplied through the compressed air inlet line 178 and flows through the proportional solenoid valve 188 which controls the flow rate, and through the inlet solenoid valve 190 which controls time with the outlet solenoid valve 192 closed. Afterwards, compressed air flows through the cross fitting 180 to a cavity below the inhalation diaphragm 126 and to a cavity above the exhalation diaphragm 152. This causes the diaphragms 126, 152 to expel air contained in the other side of each diaphragm 126, 152. On the inhalation diaphragm 126, air is expelled through a fitting and inhalation solenoid valve assembly 142 is open, and sensor assembly 144 monitors air pressure and flowrate or oxygenated air delivered to the patient. At the same time, air from previous exhalation in lower cavity of exhalation diaphragm 152 is expelled through a fitting and through exhalation check valve assembly 164.

During exhalation mode, as the inhalation and exhalation diaphragms 126, 152 reach their top and bottom positions respectively, solenoid valves 142, 190 close and solenoid valves 160, 192, open permitting compressed air to escape through compressed air outlet 184 allowing diaphragms 126, 152 to return to their center positions, with diagram 126 sucking fresh air through inhalation check valve assembly 134, and diaphragm 152 discharging air from patient. In a case that more volume capacity is required, outlet 184 can be connected to a vacuum line so diaphragms 126, 152 will move beyond their middle position and draw more air—fresh for inhalation and spent from exhalation. In other embodiments, diaphragms 126, 152, may include a coil spring attached to their centers on one end, and attached to the inner center of housings 122 and 148, making them return beyond their respective center positions when solenoid valve 192 opens.

In some embodiments, the control system 8 may also include an automatic solenoid relief valve 200 (shown in FIG. 9) that is operated by the controller 67 to control excess pressure at different phases of respiratory cycle without affecting flow rate or volume. Automatic excess pressure may be reduced with a mechanical relief valve 202, with interchangeable seals precision calibrated for different pressures. The control system 8 may also include large pilot lights in two different colors to indicate if ventilator is operating in inhalation or exhalation, on display assembly 168 independent from screen, visible from several meters distance. The display assembly 168 may include a large emergency stop push button that instantaneously stops ventilator operation opening all inhalation and exhalation valves, thus allowing patient to breath from surrounding air, preventing patient choking. The control system 8 may include an instantaneous stop push button for interrupting operation in any point of respiratory cycle, and resuming instantaneously operation at stopping cycle point. This is very useful for ventilator operator for checking with more detail pressures and other parameters, and also for performing short recruitment maneuvers. The control system 8 may also include visible and audible alarms with mute mode for audible possible; measurement and displaying of spontaneous respirations percentage in ventilation modes that permit, along with mandatory, spontaneous respirations from patient, and Recruitment Maneuver easily configured and performed, with several safety features.

The diaphragms can be orientated vertically, horizontally, or offset with the following advantages: 1) Eccentric loads are avoided, simplifying mechanical design and increasing life of diaphragms and actuator; 2) The external dimensions of ventilator are greatly diminished; with diaphragms in tandem, double space is required perpendicularly to diaphragms axis; 3) In a vertical fashion, one on top of 2-rod actuator and the other in the bottom, ventilator occupies the same space or even a little less than ventilators currently in use; 4) If, during use, you want to get "spent" air from patient away from the room in which the ventilator is, it can be done but it is not necessary or usual practice; in most cases they discharge "spent" air into same room prior passage through a filter. In the design in which compressed air pushes the diaphragms, if you have available a vacuum line it would double ventilator capacity. This means that the ventilator could be smaller for a certain capacity than without a vacuum line. It is because without a vacuum line after inspiration, diaphragm returns to its central position, and with a vacuum line it would return all the way down to the opposite casket, in fact duplicating air volume displaced; and 5) can arrange stacked diaphragms horizontally or vertically. This can also be achieved with the coil spring as described above.

Additional benefits of the respiratory ventilator system 10 include: 1) Ease of fabrication in a minimally equipped metal fabricating shop. 2) Fabrication can be initiated almost immediately because no special tooling is required. 3) Replicates the natural human breathing mechanism, both in inhalation and exhalation, which will surely prove to be of therapeutic benefit. 4) All necessary parts and equipment such as valves, switches, pneumatic cylinder, fittings, tubing, timers, adjustable automatic slide, etc. are low cost and manufactured massively, and many companies carry them in stock. 5) Simple design that facilitates maintenance or repair easily and with basic electricity and mechanics knowledge. 6) Respiratory volume and frequency easily adjustable. 7) Simultaneous and or parallel use of diaphragms or any other air injection/extraction mechanism for inhalation and exhalation. 8) Use of any kind of three dimensional figure both regular and or irregular—cylinder, cube, prism, cone, pyramid, etc. with a diaphragm attached to perform, simultaneously or not, inhalation and exhalation functions. 9) Use of any kind of elastic material, natural or synthetic, in any shape, simultaneously or alternatively for reproducing the natural mechanism of human breathing. 10) Minimum risk of supplying or extracting air with excessive pressure or vacuum to the patient.

The respiratory ventilator device 2 also provides reconfiguration or redesign of two-diaphragm pumps to work as previously described ventilator device with the placement of diaphragms on the same axle, vertical, horizontal and otherwise, and also in a tandem configuration. The respiratory ventilator device 2 may also use any air or fluid movement device (e.g. apparatus, machine other than diaphragms such as fans, turbines, bellows, pumps, etc.) to work in the same two movements sequence of operation of the ventilator device herein described: first movement, in injection inhalation-side, fresh air is moved, blown, and/or impulsed towards patient and simultaneously spent air, that is extracted from patient in previous movement, is expelled from device in extraction exhalation-side. In second movement, fresh air is suctioned, blown, and/or impulsed, injected into chamber on injection side, and simultaneously exhaled air from patient is suctioned, extracted, into chamber on extraction side.

The respiratory ventilator device 2 also provides 1) ease of fabrication; practically all components can be purchased from stock or easily made in a metal working shop with basic metal working equipment; 2) Inhalation and exhalation mechanisms are almost equal to human respiration mechanism; 3) No motors, fans, bellows or actuators; 4) No mechanisms to convert circular motion to reciprocating; 5) Minimum moving parts which makes it more reliable and durable; 6) Control equipment and components are of common use throughout the world in several industries, which makes it cheaper, reliable, and easily replaceable; and 7) simplicity which reduces downtime for repairs and maintenance.

A controller, computing device, or computer, such as described herein, includes at least one or more processors or processing units and a system memory. The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Other aspects and features of the present invention can be obtained from a study of the drawings, the disclosure, and the appended claims. The invention may be practiced otherwise than as specifically described within the scope of the appended claims. It should also be noted, that the steps and/or functions listed within the appended claims, notwithstanding the order of which steps and/or functions are listed therein, are not limited to any specific order of operation.

The above description of illustrated examples of the present invention are not intended to be exhaustive or to be limitation to the precise forms disclosed. While specific embodiments of, and examples for, the invention are described herein for illustrative purposes, various equivalent modifications are possible without departing from the broader spirit and scope of the present invention.

What is claimed is:

1. A respiratory ventilator device, comprising:
   an inhaled air assembly coupled to a patient respiratory circuit and configured to channel a volume of inhalation air to a patient's lungs via the patient respiratory circuit to assist in patient inhalation, the inhaled air assembly including an injector diaphragm assembly coupled between the patient respiratory circuit and a supply of oxygenated air for receiving the volume of inhalation air from the supply of oxygenated air and delivering the volume of inhalation air to the patient respiratory circuit, the injector diaphragm assembly including:
   an injector diaphragm housing including a cylindrical tank having an inner surface defining an inhalation air chamber and an injector volume reduction member positioned within an interior of the cylindrical tank for reducing an internal volume of the inhalation air chamber; and
   an inhalation diaphragm coupled to the injector diaphragm housing to enclose the inhalation air chamber, the inhalation diaphragm including a flexible silicone rubber assembly attached to an open top end of the cylindrical tank and moveable between a first inhalation position and a second inhalation position to adjust the internal volume of the inhalation air chamber;
   an exhaled air assembly coupled to the patient respiratory circuit and configured to remove air from the patient's lungs via the patient respiratory circuit to assist in a patient exhalation, the exhaled air assembly including an extractor diaphragm assembly coupled between the patient respiratory circuit and an exhaust air outlet connector assembly for receiving a volume of exhaled air from the patient respiratory circuit and delivering the volume of exhaled air to the exhaust air outlet connector assembly, the extractor diaphragm assembly including:
   an extractor diaphragm housing including an inner surface defining an exhalation air chamber; and
   an exhalation diaphragm coupled to the extractor diaphragm housing to enclose the exhalation air chamber, the exhalation diaphragm moveable between a first exhalation position and a second exhalation position to adjust a volume of the exhalation air chamber; and
   a control system operatively coupled to the inhaled air assembly and the exhaled air assembly and configured to operate the respiratory ventilator device in an inhalation mode and an exhalation mode;
   wherein the control system operates the inhaled air assembly to generate a positive air pressure to channel the volume of inhalation air to the patient's lungs during the inhalation mode; and
   wherein the control system operates the exhaled air assembly to generate a negative air pressure to remove the air from the patient's lungs during the exhalation mode.

2. The respiratory ventilator device of claim 1, wherein the control system operates the exhaled air assembly to channel the air removed from the patient's lungs to an exhaust air outlet connector assembly during the inhalation mode.

3. The respiratory ventilator device of claim 2, wherein the control system operates the inhaled air assembly to receive the volume of inhalation air from the supply of oxygenated air during the exhalation mode.

4. The respiratory ventilator device of claim 3, wherein the injector volume reduction member includes a comic member positioned inside the cylindrical tank of the injector diaphragm housing for reducing the internal volume of injector cylindrical tank.

5. The respiratory ventilator device of claim 1, wherein the extractor diaphragm housing includes a second cylindrical tank having an inner surface defining the exhalation air chamber and an extractor volume reduction member positioned within an interior of the second cylindrical tank for reducing an internal volume of the exhalation air chamber; and
   wherein the exhalation diaphragm includes a second flexible silicone rubber assembly attached to an open top end of the second cylindrical tank and moveable between the first exhalation position and the second exhalation position to adjust the volume of the exhalation air chamber.

6. The respiratory ventilator device of claim 1, wherein the inhalation air chamber defines a first volume of the inhalation air chamber with the inhalation diaphragm in the first inhalation position and defines a second volume of the inhalation air chamber with the inhalation diaphragm in the second inhalation position, the first volume of the inhalation air chamber being greater than the second volume of the inhalation air chamber.

7. The respiratory ventilator device of claim 6, wherein the injector diaphragm assembly includes:
   an inhalation inlet line coupled to the injector diaphragm housing and configured to receive the volume of inhalation air from the supply of oxygenated air into the injector diaphragm housing;
   an inhalation check valve assembly coupled to the inhalation inlet line;
   an inhalation outlet line coupled to the injector diaphragm housing and configured to deliver the volume of inhalation air to the patient respiratory circuit from the injector diaphragm housing; and
   an inhalation solenoid valve assembly coupled to the inhalation outlet line and configured to selectively channel oxygenated air from the injector diaphragm housing to the patient respiratory circuit.

8. The respiratory ventilator device of claim 7, wherein the exhalation air chamber defines a first volume of the exhalation air chamber with the exhalation diaphragm in the first exhalation position and defines a second volume of the exhalation air chamber with the exhalation diaphragm in the second exhalation position, the first volume of the exhalation air chamber being greater than the second volume of the exhalation air chamber.

9. The respiratory ventilator device of claim 8, wherein the exhaled air assembly includes:
- an exhalation inlet line coupled to the extractor diaphragm housing and configured to receive the volume of exhaled air from the patient respiratory circuit into the extractor diaphragm housing;
- an exhalation solenoid valve assembly coupled to the exhalation inlet line and configured to selectively channel exhaled air from the patient respiratory circuit into the extractor diaphragm housing;
- an exhalation outlet port coupled to the extractor diaphragm housing and configured to deliver the volume of exhaled air to the exhaust air outlet connector assembly; and
- exhalation check valve assembly coupled between the extractor diaphragm housing and the exhaust air outlet connector assembly.

10. The respiratory ventilator device of claim 8, wherein the control system operates the inhaled air assembly and the exhaled air assembly in an operating cycle including a compression phase and an expansion phase.

11. The respiratory ventilator device of claim 10, wherein the control system operates the inhaled air assembly and the exhaled air assembly in the compression phase by:
- moving the inhalation diaphragm from the first inhalation position to the second inhalation position to reduce the volume of the inhalation air chamber to deliver the volume of inhalation air to the patient respiratory circuit; and
- moving the exhalation diaphragm from the first exhalation position to the second exhalation position to reduce the volume of the exhalation air chamber and deliver the volume of exhaled air to the exhaust air outlet connector assembly.

12. The respiratory ventilator device of claim 11, wherein the control system operates the inhaled air assembly and the exhaled air assembly in the expansion phase by:
- moving the inhalation diaphragm from the second inhalation position to the first inhalation position to increase the volume of the inhalation air chamber to receive the volume of inhalation air from the supply of oxygenated air; and
- moving the exhalation diaphragm from the second exhalation position to the first exhalation position to increase the volume of the exhalation air chamber to remove the air from the patient's lungs.

13. The respiratory ventilator device of claim 12, wherein the control system includes a pneumatic compressed air assembly coupled to the inhaled air assembly and the exhaled air assembly for operating the inhaled air assembly and the exhaled air assembly through the compression phase and the expansion phase.

14. The respiratory ventilator device of claim 12, wherein the control system includes a reciprocating assembly coupled to the inhaled air assembly and the exhaled air assembly for operating the inhaled air assembly and the exhaled air assembly through the compression phase and the expansion phase.

15. A method of operating a respiratory ventilator device including an inhaled air assembly coupled between a supply of oxygenated air and a patient respiratory circuit and an exhaled air assembly coupled between the patient respiratory circuit and an exhaust air outlet connector assembly, the method including:
- operating the inhaled air assembly to generate a positive air pressure to channel a volume of inhalation air to the patient's lungs during an inhalation mode, the inhaled air assembly including an injector diaphragm assembly coupled between the patient respiratory circuit and the supply of oxygenated air for receiving the volume of inhalation air from the supply of oxygenated air and delivering the volume of inhalation air to the patient respiratory circuit, the injector diaphragm assembly including an injector diaphragm housing and an inhalation diaphragm coupled to the injector diaphragm housing, the injector diaphragm housing including a cylindrical tank having an inner surface defining an inhalation air chamber and an injector volume reduction member positioned within an interior of the cylindrical tank for reducing an internal volume of the inhalation air chamber, the inhalation diaphragm including a flexible silicone rubber assembly attached to an open top end of the cylindrical tank and moveable between a first inhalation position and a second inhalation position to adjust the internal volume of the inhalation air chamber; and
- operating the exhaled air assembly to generate a negative air pressure to remove the air from the patient's lungs during an exhalation mode, the exhaled air assembly including an extractor diaphragm assembly coupled between the patient respiratory circuit and an exhaust air outlet connector assembly for receiving a volume of exhaled air from the patient respiratory circuit and delivering the volume of exhaled air to the exhaust air outlet connector assembly, the extractor diaphragm assembly including an extractor diaphragm housing including an inner surface defining an exhalation air chamber and an exhalation diaphragm coupled to the extractor diaphragm housing to enclose the exhalation air chamber, the exhalation diaphragm moveable between a first exhalation position and a second exhalation position to adjust a volume of the exhalation air chamber.

16. The method of claim 15, further comprising:
- operating the exhaled air assembly to channel the air removed from the patient's lungs to the exhaust air outlet connector assembly during the inhalation mode; and
- operating the inhaled air assembly to receive the volume of inhalation air from the supply of oxygenated air during an exhalation mode.

17. The method of claim 16, further comprising operating the inhaled air assembly and the exhaled air assembly in an operating cycle including a compression phase and an expansion phase.

18. The method of claim 16, wherein the injector volume reduction member includes a conic member positioned inside the cylindrical tank of the injector diaphragm housing for reducing the internal volume of injector cylindrical tank.

19. The method of claim 17, further comprising:
- operating the inhaled air assembly in the compression phase by moving the inhalation diaphragm to reduce a volume of the inhalation air chamber to deliver the volume of inhalation air to the patient respiratory circuit; and
- operating the exhaled air assembly in the compression phase by moving the exhalation diaphragm to reduce a volume of the exhalation air chamber to deliver the volume of exhaled air to the exhaust air outlet connector assembly.

20. The method of claim 19, further comprising:
- operating the inhaled air assembly in the expansion phase by moving the inhalation diaphragm to increase the volume of the inhalation air chamber to receive the volume of inhalation air from the supply of oxygenated air; and operating the exhaled air assembly in the expansion phase by moving the exhalation diaphragm from the second exhalation position to the first exhalation position to increase the volume of the exhalation air chamber to remove the air from the patient's lungs.

\* \* \* \* \*